(12) United States Patent
Champagne et al.

(10) Patent No.: US 10,947,604 B2
(45) Date of Patent: Mar. 16, 2021

(54) REMOTE ACCESS SYSTEM AND METHOD FOR PLANT PATHOGEN MANAGEMENT

(71) Applicant: 9087-4405 QUÉBEC INC., Joliette (CA)

(72) Inventors: Michel Champagne, Saint-Félix-de-Valois (CA); Christian Lebeau Jacob, Saint-Lin-Laurentides (CA); Sonia Desjardins, Saint-Norbert (CA)

(73) Assignee: 9087-4405 QUEBEC INC., Joliette (CA)

( * ) Notice: Subject to any disclaimer, the term of this patent is extended or adjusted under 35 U.S.C. 154(b) by 14 days.

(21) Appl. No.: 15/609,726

(22) Filed: May 31, 2017

(65) Prior Publication Data
US 2017/0349957 A1  Dec. 7, 2017

Related U.S. Application Data

(60) Provisional application No. 62/344,064, filed on Jun. 1, 2016.

(30) Foreign Application Priority Data

Nov. 15, 2016  (WO) ................ PCT/CA2016/051326

(51) Int. Cl.
*A01N 63/04* (2006.01)
*C12R 1/645* (2006.01)
(Continued)

(52) U.S. Cl.
CPC .............. *C12R 1/645* (2013.01); *A01N 25/00* (2013.01); *A01N 63/30* (2020.01); *C12N 1/14* (2013.01); *C12N 1/00* (2013.01)

(58) Field of Classification Search
CPC .......... A01N 63/04; A01N 25/00; C12N 1/00; C12N 1/14; C12R 1/645
See application file for complete search history.

(56) References Cited

U.S. PATENT DOCUMENTS 4,683,195 A  7/1987  Mullis et al.
4,683,202 A  7/1987  Mullis
(Continued)

FOREIGN PATENT DOCUMENTS

EP       0320308      6/1989
WO   WO 2007062442   6/2007

OTHER PUBLICATIONS

Azfar et al., "Pest detection and control techniques using wireless sensor network", Journal of Entomology and zoology studies, vol. 3(2), pp. 92-99, Apr. 2015.
(Continued)

*Primary Examiner* — Shogo Sasaki
(74) *Attorney, Agent, or Firm* — Kilpatrick Townsend & Stockton LLP

(57) ABSTRACT

Remote access methods and systems for plant pathogen (e.g., fungi or fungus-like organisms) assessment and management, and uses thereof, in particular for real-time agricultural applications, are described herein. In embodiments, the method and systems combine the capture of pathogenic spores (e.g., by impaction on an adhesive surface), laboratory analysis to identify the spores (e.g., by microscopy and/or PGR), collecting weather data, determining the level of risk for each pathogen, and providing an output to a user, who may for example access such risk data remotely as a risk report. A weather station is installed in proximity to the field/area where the spore sampling/collection occurs, and allows the constant transfer of weather data to effect the risk assessment. The risk assessment may be used to direct and
(Continued)

optimize pesticide (e.g., fungicide) application in accordance with the pathogen identification and assessed risk level.

22 Claims, 8 Drawing Sheets

(51) Int. Cl.
  *A01N 25/00*    (2006.01)
  *A01N 63/30*    (2020.01)
  *C12N 1/14*     (2006.01)
  *C12N 1/00*     (2006.01)

(56) References Cited

U.S. PATENT DOCUMENTS

| | | | |
|---|---|---|---|
| 4,786,600 | A | 11/1988 | Kramer et al. |
| 4,800,159 | A | 1/1989 | Mullis et al. |
| 5,422,252 | A | 6/1995 | Walker et al. |
| 6,087,133 | A | 7/2000 | Dattagupta et al. |
| 6,124,120 | A | 9/2000 | Lizardi |
| 6,387,652 | B1 * | 5/2002 | Haugland ............... C12Q 1/689 435/254.1 |
| 6,463,814 | B1 | 10/2002 | Letarte et al. |
| 7,291,465 | B2 | 11/2007 | Karaolis |
| 7,370,543 | B2 | 5/2008 | Chen et al. |
| 7,659,067 | B2 | 2/2010 | Dean et al. |
| 9,324,067 | B2 | 4/2016 | Van Os et al. |
| 9,580,760 | B2 * | 2/2017 | Oppedahl ................. C12N 1/14 |
| 2003/0099946 | A1 * | 5/2003 | Barnett ................ C12Q 1/6895 435/6.15 |

OTHER PUBLICATIONS

Datir, Sakita et al., "Monitoring and Detection of Agricultural Disease using Wireless Sensor Network", International Journal of Computer Applications, vol. 87-No. 4, Feb. 2014.
Abad, G., Methods for identification of *Phytophthora* species, Workshop: Fighting Phytophthora: How to Detect, Investigate, and Manage Phytophthora, APS Cenntennial Meeting, Jul. 26, 2008.
AlShahni et al., Direct colony PCR of several medically important fungi using Ampdirect® Plus, Jpn. J. Inect. Dis. 62: 164-167, 2009.
Broome et al., Development of an infection model for Botrytis bunch rot of grapes base on wetness duration and temperature, Phytopathology 85(1): 97-102, 1995.
Caffi et al., A model predicting primary infections of plasmopara viticola in different grapevine-growing areas of Italy, Journal of Plant Pathology 91(3): 535-548, 2009.
Cao et al., Development of Weather and Airbone Inoculum-Based Models to Describe Disease Severity and Wheat Powdery Mildew, Plant Disease, vol. 99(3): 395-400, 2015.
Chilvers et al., Detection and Identification of *Botrytis* Species Associated with Neck Rot, Scape Blight, and Umbel Blight of Onion, Plant Health Progress doi:10.1094, Nov. 27, 2006.
De Visser, Development of a downy mildew advisory model based on downcast, Eur. J. Plant Pathol., 104: 933-943, 1998.
Drenth and Sendall, Practical guide to detection and identification of Phytophthora, CRC for Tropical Plant Protection, Brisbane, Australia, Jun. 2001.
Dvorak et al., Detection of airborne inculum of Hymenoscyphus fraxineus and H. albidus during seasonal fluctuations associated with absence of apothecia, Forests, vol. 7(1): 1-13, 2016.
Gerrettson-Cornell, A compendium and classification of the species of the genus *Phytopphthora de bary* by the canons of the traditional taxonomy, Technical Paper No. 45, Research Division, State Forests of New South Wales, Sydney, Australia, Aug. 1994.
Gilles et al., Development of Milioncast, an improved model for predicting downy mildew sporulation on onions, Plant disease, 88: 695-702, 2004.
Inglesias et al., Evaluation of the different Alternaria prediction models on a potato crop in a Limia (NW of Spain), Aerobiologia 23: 27-34, 2007.
Kwoh et al., Transcription-based amplification system and detection of amplified human immunodeficiency virus type 1 with a bead-based sandwich hybridization format, Proc. Natl. Acad. Sci. USA 86: 1173-1177, 1989.
Latorse et al., Molecular Analysis of Alternaria Populations Early Blight Causal Agents in Potato Plants, Twelfth EuroBlight workshop, Arras, France, PPO-Special Report No. 14: 179-186, 2010.
Leiminger et al., Quantification of disease progression of *Alternaria* spp. on potato using real-time PCR, Eur. J. Plant Pathol. 141: 295-309, 2015.
Lindsley et al., A two-stage cyclone using microcentrifuge tubes for personal bioaerosol sampling. J. Environ. Monit. 8:1136-42, 2006.
Llorente et al., Evaluation of BSPcast Disease Warning System in Reduced Fungicide Use Programs for Management of Brown Spot of Pear, Plant Disease 84(6): 631-637, 2000.
Madsen, Effects of Airflow and Changing Humidity on the Aerosolization of Respirable Fungal Fragments and Conidia of Botrytis cinereal, Applied and Environmental Microbiology 78(11): 3999-4007, 2012.
Mirazaei et al., Identification of *Botrytis* spp. on Plants Grown in Iran, J. Phytophathol. 156: 21-28, 2008.
Montesinos et al., Development and evaluation of an infection model for Stemphylium vesicarium on pear based on temperature and wetness duration, Phytopathology 85(5): 586-592, 1995.
Prabha et al., A simple method for total genomic DNA extraction from water moulds, Current Science, 104(3): 345-347, 2013.
Savage et al., Mobile traps are better than stationary traps for surveillance of airborne fungal spores, Crop Protection 36: 23-30, 2012.
Vincelli and Lorbeer, Forecasting spore episodes of Botrytis squamosa in commercial onion fields in New York, Phytopathology 78(7): 966-970, 1988.
Von Wahl and Kersten, Fusarium and Didymella—neglected spores in the air, Aerobiologia 7: 111-117, 1991.
Wharton et al., Fusarium dry rot, Michigan State University Extension Bulletin E-2992, May 2007.
ISR and WO—PCT/CA2016/051326, 2017.
Office Action dated Aug. 29, 2017 in CA 2,969,282.
Office Action dated Oct. 17, 2017 in CA 2,969,282.
West, J.S. et als, Innovations in air sampling to detect plant pathogens, Ann Appl Bid 166 (2015) 4-17.
Fall, M.L. et als, Spatiotemporal variation in airborne sporangia of Phytophthora infestans: characterization and initiatives towards improving potato late blight risk estimation, Plant Pathology (2015) 64, 178-190.
Taylor, M.C, et als, Relative performance of five forecasting schemes for potato late blight (*Phytophthora infestans*) I.Accuracy of infection warnings and reduction of unnecessary, theoretical, fungicide applications, Crop Protection 22 (2003) 275-283.
Datir, Sarika, Monitoring and Detection of Agricultural Disease using Wireless Sensor Network, International Journal of Computer Applications (0975-8887) vol. 87-No. 4, Feb. 2014.
Van Der Heyden, Hervey et als, Comparison of monitoring based indicators for initiating fungicide spray programs to control Botrytis leaf blight of onion, Crop Protection 33 (2012) 21-28.

* cited by examiner

Proliferation Index

| Sample(s) | Residue | Mold and/or Bacteria | | Quantity (PFT/m3) | | | Risk | |
|---|---|---|---|---|---|---|---|---|
| | | Identification | Associated Disease | Previous | | Actual | Previous | Actual |
| Grapevine | 0 | Erysiphe necator | Oïdium | ND | ND | 3 | 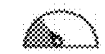  |  |
| | | Alternaria alternata | Alternaria disease | ND | ND | 1 | 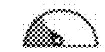  |  |
| | | Botrytis cinerea | Noble rot | ND | ND | 3 | 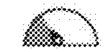  |  |
| | | Plasmopara viticola | Mildew | ND | ND | 4 |  |  |
| Field No. 5 | 0 | Phytophthora infestans | Mildew | ND | 1 | 1 |  |  |
| Onion field | 0 | Botrytis squamosa | Grey rot | ND | 2 | 3 | 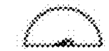  |  |
| | | Pernospora destructor | Mildew | ND | 1 | 3 | 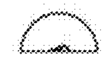  |  |
| | | Fusarium spp. | Fusarium infection | ND | ND | 1 | 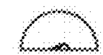  |  |

Legend of proliferation risk according to weather conditions

Not available Low Risk Medium Risk High Risk

Note: In this report you will find two indications for decision-making: the number of observed spores and the weather conditions specific to the proliferation of specific molds associated with the spores.

Residue scale

0: No residue
1-2: Low amount of residue. Negligible or low interference with risk assessment.
3-4: Medium amount of residue. Sample analysis may be compromised.
5: High amount of residue. Sample analysis is inadequate.

FIG. 3

REMOTE ACCESS SYSTEM AND METHOD FOR PLANT PATHOGEN MANAGEMENT

CROSS REFERENCE TO RELATED APPLICATIONS

The present application claims the benefit of U.S. Provisional Application Ser. No. 62/344,064 filed on Jun. 1, 2016, and of PCT International Application No. PCT/CA2016/051326 filed on Nov. 15, 2016, both of which are incorporated herein by reference in their entirety.

FIELD OF THE INVENTION

The present invention relates to remote access methods and systems for plant pathogen assessment and management, and uses thereof, in particular for real-time agricultural applications.

BACKGROUND OF THE INVENTION

Diseases in plants caused by pathogens result in considerable crop loss from year to year, resulting both in economic loss and shortfalls in food production. Fungi are the number one cause of crop loss worldwide. Viruses, nematodes, and bacteria also cause diseases in plants. The widespread use of fungicides has assisted in reducing plant disease. However, fungicides are not always used in an optimal manner, as they are for example not always correctly targeted to the plant pathogen in question, are often only applied after disease symptoms appear, and/or may be over-applied leading to unnecessary use which in turn increases their cost and environmental impact.

Thus, there remains a need for improved methods of plant pathogen assessment and management, to assist in the identification of the risk of plant pathogen infection and disease, and in turn direct appropriate and efficient pesticide (e.g., fungicide) treatment.

The present description refers to a number of documents, the content of which is herein incorporated by reference in their entirety.

SUMMARY OF THE INVENTION

The present invention relates to methods and systems for pathogen assessment and management and uses thereof, in particular for remote real-time agricultural applications. In particular, the methods and systems described herein may be used to identify pathogens in an agricultural area and provide a real-time risk assessment of pathogen infection and related disease in plants or crops in the agricultural area. The nature and the integration of the different sources of data collection and output generation allows a user to remotely access such risk assessment in a rapid and timely manner. With such risk assessment, agricultural producers can for example optimize fungicide treatment, applying the right fungicide for the identified pathogen(s) and at the appropriate time for optimal and effective use, not only resulting in effective prevention and treatment of pathogen-based plant disease, but also reducing the costs and environmental impact of increased or unnecessary fungicide use.

The methods and systems described herein have been effectively tested for outdoor use in the agricultural applications described herein.

According to the present invention, there is provided a method for microbiological assessment of pathogens, comprising:

capturing pathogenic spores by means of a spore collector in an agricultural area adapted to cultivate at least one plant or crop variety;

identifying the pathogenic spores captured by the spore collector and generating pathogenic spore data;

collecting weather data in proximity of the agricultural area;

calculating a risk assessment to the plant or crop variety based on the pathogenic spore data and the weather data; and informing a user of the risk assessment.

According to another aspect of the present invention, there is provided a system for microbiological assessment of pathogens, comprising a spore collector for capturing pathogenic spores in an agricultural area adapted to cultivate at least one plant or crop variety;

microbiological spore identifying means for identifying the pathogenic spores captured by the spore collector;

a weather station for collecting weather data in proximity of the agricultural area; and a controller comprising a processor and a memory configured to:

receive pathogenic spore data that is obtained from the microbiological spore identifying means;

receive weather data collected from the weather station;

calculate a risk assessment to the plant or crop variety based on the pathogenic spore data and the weather data; and transmit an output containing the risk assessment for display to a user.

According to another aspect of the present invention, there is provided a system for microbiological assessment and suppression of pathogens, comprising:

a spore collector for capturing pathogenic spores in an agricultural area adapted to cultivate at least one plant or crop variety;

microbiological spore identifying means for identifying the pathogenic spores captured by the spore collector;

a weather station for collecting weather data in proximity of the agricultural area; and a controller comprising a processor and a memory configured to:

receive pathogenic spore data that is obtained from the microbiological spore identifying means;

receive weather data collected from the weather station;

calculate a risk assessment to the plant or crop variety based on the pathogenic spore data and the weather data, wherein the risk assessment is calculated in real-time with respect to the pathogenic spore data and weather data that are received by the controller; and pathogenic control means for spraying the plant variety or crop with an anti-pathogenic substance based on the risk assessment.

According to another aspect of the present invention, there is provided a computer-readable storage medium having computer-readable code embedded therein, which, when loaded in and executed by a computing device, causes the computing device to perform the steps of:

receiving pathogenic spore data that is obtained from a microbiological spore identifying means;

receiving weather data collected from a weather station;

calculating a risk assessment to a plant or crop variety based on the pathogenic spore data and the weather data; and transmitting the risk assessment to a user.

In embodiments, the spore collector is positioned in the agricultural area such that the wind passes over at least a portion of the agricultural area before reaching the spore collector.

In embodiments, the spore collector is positioned at least 1 m above the ground and at least 0.15 m above plant foliage.

In embodiments, the spore collector is part of a portable sampling kit.

In an embodiment, the plant is a tuber. In a further embodiment, the plant is potato.

In an embodiment, the plant is of the genus *Allium*. In a further embodiment, the plant is onion.

In an embodiment, the plant is a carrot.

In an embodiment, the plant is a grapevine.

In embodiments, the pathogen is a fungus or a fungus-like organism. In further embodiments, the fungus is an ascomycete, a basidiomycete or a deuteromycete. In further embodiments, the fungus-like organism is an oomycete or a phytomoxea.

In an embodiment, the pathogenic spores are captured by impaction, by air filtration or by deposition via vortex or in a low pressure chamber.

In an embodiment, the pathogenic spores are captured at an airflow of about 10 to about 20 L air/minute, in a further embodiment, at an airflow of about 15 L air/minute.

In an embodiment, the capturing of the pathogenic spores is for a period of about 5 to about 20 minutes, in a further embodiment, for a period of about 15 minutes.

In an embodiment, the identification of the spores is by optical microscopy.

In an embodiment, the identification of the spores is by an amplification method. In a further embodiment, the amplification is by a polymerase chain reaction (PCR, Q-PCR, VNTR, etc.).

In embodiments, the weather data comprises one or more of (i) temperature, (ii) humidity, (iii) rainfall, (iv) pressure (v), dewpoint, (vi) continuous duration of any one of (i)-(v), or (vii) time of day of occurrence of any one of (i)-(v).

In an embodiment, the pathogenic spore data is generated in a remote location relative to the agricultural area.

In an embodiment, the pathogenic spore data is generated in a remote location relative to the user.

In an embodiment, the risk assessment is calculated in a remote location relative to the agricultural area.

In an embodiment, the risk assessment is calculated in a remote location relative to the user.

In an embodiment, the user is located in a remote location relative to the agricultural area.

In an embodiment, the controller is located in a remote location relative to the agricultural area.

In an embodiment, the controller is located in a remote location relative to the user.

In an embodiment, the system comprises a computer device for receiving the output of the controller, the computer device being located in a remote location relative to the agricultural area.

In an embodiment, the pathogenic control means comprises a robotic device for receiving instructions from the controller to automatically spray the plant variety or crop with the anti-pathogenic substance based on the risk assessment.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 3 is a schematic view of a partial risk assessment report transmitted to a user, according to a preferred embodiment of the present invention.

DESCRIPTION OF ILLUSTRATIVE EMBODIMENTS

Figure 1A:
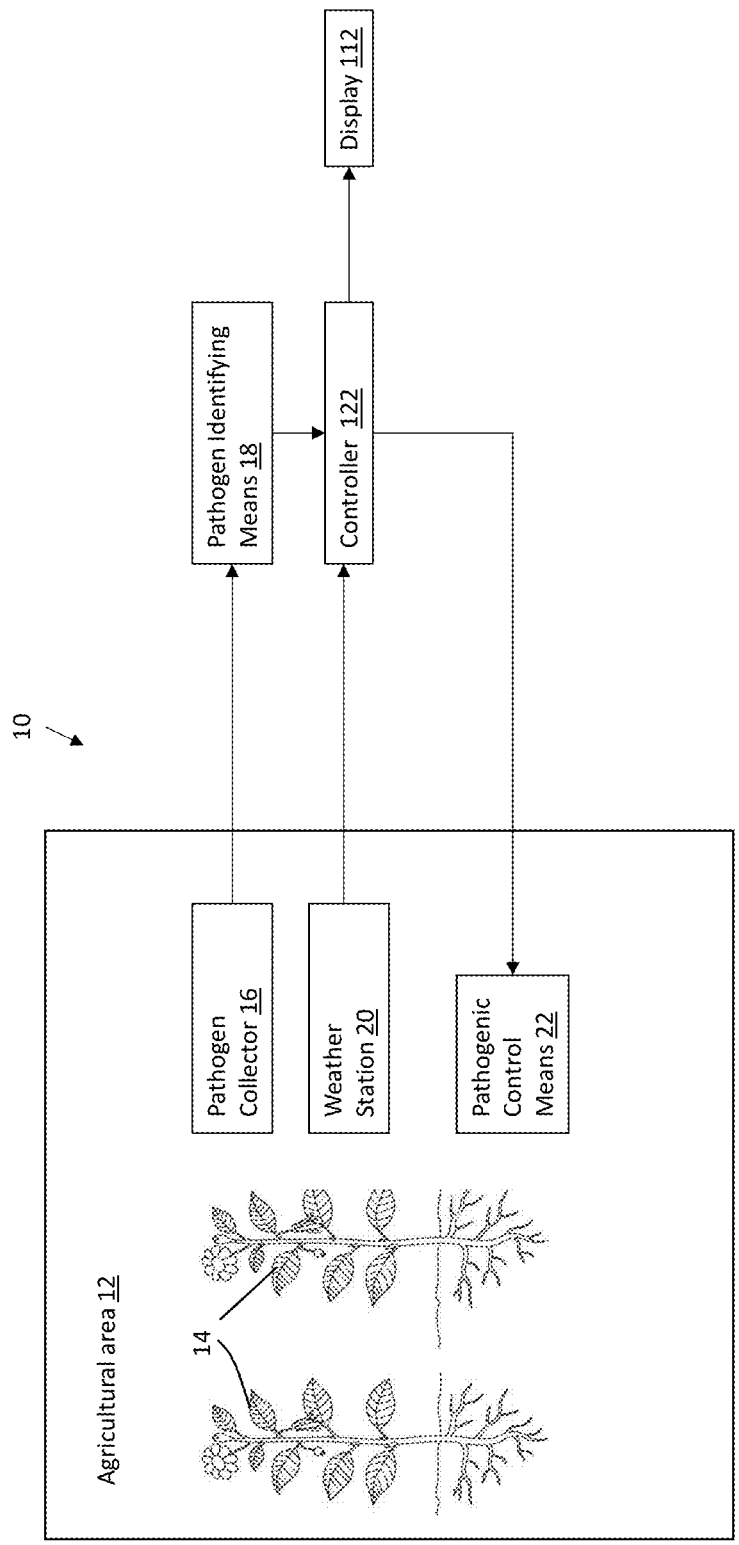
FIG. 1A is a block diagram of a pathogen management system, according to an embodiment of the present invention.

Described herein are methods and systems for microbiological assessment of pathogens. In an embodiment, the methods and systems are for assessment of plant pathogens in agricultural applications. In embodiments, the method and systems combine the capture of pathogenic spores (e.g., by impaction on an adhesive surface), laboratory analysis to identify the spores (e.g., by microscopy and/or KR), collecting weather data, determining the level of risk for each pathogen, and providing an output to a user, who may for example access such risk data remotely as a risk report: For example, if the capture of spores takes place three times a week, a risk report can be received by the user every two or three days, which are available directly on the remote application interface: A weather station is installed in proximity to the field/area where the spore sampling occurs, and allows the constant transfer of weather data to effect the risk assessment.

General Definitions

As used herein, the terms "a" and "an" and "the" and similar referents in the context of describing the invention (especially in the context of the following claims) are to be construed to cover both the singular and the plural, unless otherwise indicated herein or clearly contradicted by context.

As used herein, the terms "comprising", "having", "including", and "containing" are to be construed as open-ended terms (i.e., meaning "including, but not limited to") unless otherwise noted.

As used herein, the term "consists of" or "consisting of" means including only the elements, steps, or ingredients specifically recited in the particular claimed embodiment or claim.

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of any and all examples, or exemplary language (e.g., "such as") provided herein, is intended merely to better illustrate the invention and does not pose a limitation on the scope of the invention unless otherwise claimed.

No language in the specification should be construed as indicating any non-claimed element as essential to the practice of the invention.

Terms and symbols of genetics, molecular biology, biochemistry and nucleic acids used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All technical and scientific terms used herein are to be understood with their typical meanings established in the relevant art.

Plant Pathogens and Associated Diseases

The methods and systems described herein may be used for the assessment of plant pathogens in agricultural applications, in an embodiment, the plant pathogen is a eukaryote. In embodiments, the plant pathogen is a fungus or a fungus-like organism. In embodiments, the fungus is an ascomycete, a basidiomycete or a deuteromycete. In embodiments, the fungus-like organism is an oomycete or phytomyxea. In embodiments, fungi and fungus-like organisms, and the related plant disease, include the following, or any combination thereof:

Ascomycetes:
*Alternaria* spp., e.g. *Alternaria alternata* (potato blight, leaf spot disease), *Alternaria solani* (early blight in potato and tomato), *Alternaria dauci* (*Alternaria* leaf blight of carrots)
*Botrytis* spp., e.g., *Botrytis cinerea* (grey mold)
*Colletotrichum* spp., e.g., *Colletotrichum coccodes/Colletotrichum atramentarium* (potato black dot)
*Cercospora* spp. (leaf spots), e.g. *Cercospora carotae* (*Cercospora* of carrots)
*Epicoccum* spp.
*Erysiphe* spp. (powdery mildew), e.g. *Erysiphe heraclei* (powdery mildew of carrot), *Erysiphe necator* (also known as *Uncinula necator*, powdery mildew of grape)
*Stemphylium* spp., e.g. *Stemphylium solani* (leaf blight in onion; also infects tomatoes, potatoes, peppers, garlic and cotton)
*Fusarium* spp. (*Fusarium* wilt disease), e.g. *Fusarium oxysporum*
*Thielaviopsis* spp. (canker rot, black root rot, *Thielaviopsis* root rot)
*Verticillium* spp.
*Magnaporthe grisea* (rice blast)
*Sclerotinia* spp., e.g., *Sclerotinia sclerotiorum* (white mold)

Basidiomycetes
*Ustilago* spp. (smut)
*Rhizoctonia* spp.
*Phakospora pachyrhizi* (soybean rust)
*Puccinia* spp. (severe rusts of most cereal grains and cultivated grasses)
*Armillaria* spp. ("honey fungus" species; virulent pathogens of trees)

Oomycetes
*Phytophthora* spp. (mostly pathogens of dicotyledons; produces mildew), e.g., *Phytophthora infestans* (potato late blight; destruction of solanaceous crops such as tomato and potato), *Phytophthora sojae* (soya bean root and stem rot)
*Pythium* spp.
*Peronospora* spp. (mildew), e.g. *Pernospora destructor* (pathogen of *Allium,* e.g. onion, shallot, chives, leek)
*Plasmopora* spp., e.g., *Plasmopora viticola* (grapevine downy mildew)

Phytomoxea
*Plasmodiaphora* spp. (dub root in cabbage)
*Spogospora* spp. (powdery scab in potatoes)

Various plant diseases and related symptoms fall into a number of categories, including rot, rust, club root, smut, mildew, blight, spots, scab and wilt.

Plants

In embodiments, the methods and systems described herein may be used to assess the risk of pathogenic infection of a variety of plants, including monocotyledonous and dicotyledonous plants. In embodiments the plants of interest include vegetables, oil-seed plants, leguminous plants, ornamentals, and conifers. Plant species of interest include for example corn (*Zea mays*), *Brassica* spp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), *Allium* spp. (onion, shallot, chives, leek), carrot (*Daucus* spp., e.g. *Daucus carota*), grapevines (*Vitis* spp.) cassaya (*Manihot esculenta*), coffee (*Coffea* spp.), coconut (*Cocos nucifera*), pineapple (*Ananas comosus*), citrus trees (*Citrus* spp.), apple (*Malus* spp.) cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Vegetables include tomatoes (*Lycopersicon lycopersicon*), lettuce (e.g., *Lactuca sativa*), green beans (*Phaseolus vulgaris*), lima beans (*Phaseolus limensis*), peas (*Lathyrus* spp.), *Cucumis* spp. such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include, for example, pines such as loblolly pine (*Pinus taeda*), slash pine (*Pinus elliotii*), ponderosa pine (*Pinus* ponderosa), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In an embodiment, the plant is of the family Solanaceae, in a further embodiment of the genus *Solanum*. In embodiments, the plants are crop plants (for example, potato, onion, carrot, grapevines, corn, alfalfa, sunflower, *Brassica*, soybean, cotton, safflower, peanut, sorghum, wheat, millet, tobacco, etc.).

Sampling

Bioaerosol sampling may be performed by various methods and using various devices (referred to herein as a "sampling device", "sampler", "pathogen collector", "spore collector" or "collector". In a preferred embodiment, bioaerosol sampling is done by an impaction method. Several types of devices (also known as impactors) are commercially available may be used to perform an impaction, for example:

Allergenco-D cassette
Jet-spore impactor
Air-O-Cell cassette
Cyclex-D cassette
Micro 5 cassette
Rotorod sampler
Burkard type captor/sampler Another type of sampling device which may be used to perform the spore capture is a cyclone aerosol sampler (e.g., a two-stage sampler), such as the NOSH BC 251 two-stage cyclone aerosol sampler, developed by the National Institute for Occupational Safety and Health (NIOSH) of the US Centers for Disease Control and Prevention (CDC). Such a device operates by allowing the sample-containing air flow (drawn through the device by vacuum) to pass through two round chambers, typically a first tube and a smaller, second tube, before reaching a filter. When the air is pulled into each round chamber it is swirled around like a cyclone, with particles being thrown against the wads of the chambers by centrifugal force, and are thus collected in the chambers. By virtue of the size of the chambers and their inlet nozzles, large particles (about 4 µm and larger) are collected in the first, larger tube, and smaller particles (about 1 µm to about 4 µm) are collected in the second, smaller tube. Subsequently, the smallest particles (<1 µm) pass through both chambers/tubes and are collected on the filter. See for example Lindsley W G, et al., 2006, A two-stage cyclone using microcentrifuge tubes for personal bioaerosol sampling. *J. Environ. Monit.* 8:1136-42; and U.S. Pat. No. 7,370,543. See for example also U.S. Pat. No, 6,463,814, which describes a bioaerosol slit impaction sampling device.

Such devices collect airborne spores on a collection substrate, such as a glass slide with a sticky surface or directly onto a filter or in a fluid. The spore deposit area is typically referred to as a "trace". The impaction of the airborne materials is generated by airflow drawing the air into the device (e.g., often via vacuum generated from a pump). Impaction thus entails separating the particles from the air stream by using the inertia of the particles, which are in turn captured on the collection substrate in the device (e.g., glass slide or filter). Particles which cannot travel with the airstream due to theft inertia will deposit on the collection substrate. The collection efficiency of the sampling device is commonly described by the $d_{50}$ cutoff point, which is influenced by the properties of the inlet and the airflow rate. Particles having a larger $d_{50}$ (mean aerodynamic diameter) than the cutoff are more likely to exit the airstream and be deposited on the collection substrate, whereas particles having a smaller $d_{50}$ than the cutoff are more likely to pass through with the exiting airstream and thus are less likely to be deposited on the collection substrate.

In an embodiment, the sampling device is a sampler (e.g., Allergenco-D, Air-O-Cell), which has been designed for indoor use, but has been found in the methods and systems described herein to be effective for outdoor use in the agricultural applications described herein. In a preferred embodiment, the sampling device is an Allergenco-D spore trap.

In an embodiment, the sampling device has a $d_{50}$ of about 1 µm to about 5 µm, in further embodiments about 1 µm to about 2.5 µm, about 1 µm to about 2 µm, about 1 µm to about 1.7 µm, about 1.5 µm to about 3 µm, about 1.5 µm to about 2.5 µm, about 1.5 µm to about 2 µm, about 1.5 µm to about 1.9 µm, about 1.6 µm to about 1.8 µm, about 1 µm to about 2 µm, about 1.3 µm to about 1.9 µm, about 1.5 µm to about 1.9 µm, about 1 µm, about 1.3 µm, about 1.5 µm, about 1.7 µm, about 1.9 µm or about 2 µm. In an embodiment, the sampling device has a $d_{50}$ of about 1.7 µm.

In embodiments, the sampling device has a $d_{50}$ of about 5 µm to 10 µm, in further embodiments about 5 µm to about 6 µm, about 5 µm to about 7 µm, about 5 µm to about 8 µm, about 5 µm to about 9 µm, about 5 µm to about 10 µm.

In embodiments, in agricultural applications, the sampling device is located for sample collection in the agricultural area of interest such that it is at least 1 m above the ground and at least 0.15 m above plant foliage (e.g., using a tripod or stand or the like).

In embodiments, in agricultural applications, the sampling device is located for sample collection in the agricultural area of interest such that the wind (air current/movement) blows over the agricultural area of interest, or a portion thereof, prior to reaching the sampling device.

In embodiments, multiple samples are obtained from different locations in the agricultural area of interest, The number of samples is dependent, among others, upon terrain topology, the dimensions of the area to be covered, the presence of buildings or forest edges adjacent to the area of interest or the presence of low air circulation areas. In a preferred embodiment, the sampling device is mobile/portable such that it can be moved between sampling locations, to obtain multiple samples. In embodiments, multiple sampling devices may be used. In embodiments, at least 2, 3, 4, 5, 6, 7, 8, 9, 10 samples are obtained to determine a risk assessment of a given area. In embodiments, 1-10 samples are obtained to determine a risk assessment, in further embodiments, 1-5 samples are obtained to determine a risk assessment.

In an embodiment, sampling is performed at a density of one sampling location per about 40 to about 60 acres of the agricultural area, in a further embodiment, at a density of one sampling location per about 45 to about 55 acres of the agricultural area, in a further embodiment, at a density of one sampling location per about 50 acres of the agricultural area.

In an embodiment, sampling is performed during the morning hours, e.g., before noon (12 PM), e.g., between 6 AM and noon, after morning dew. This time period allows for better sampling of live spores of interest. In an embodiment, sampling is performed after the agricultural area has been sprayed or irrigated with water, in a further embodiment within 6 hrs after the agricultural area has been sprayed or irrigated with water. In an embodiment, sampling is performed after a rainy period, In an embodiment, the sampling device is positioned such that the open, sample collection side or orifice is pointing substantially upward.

In a preferred embodiment, the air being tested (e.g., in the agricultural area of interest) is drawn over the sampling device using a vacuum pump. In embodiments, the vacuum pump is calibrated to draw about 5-20 L of air/minute, in a further embodiment about 5-15 L of air/minute, in a further embodiment about 10-20 L of air/minute, in a further embodiment about 12-18 L of air/minute, in a further embodiment about 14-16 L of air/minute, in further embodiments about 5, 6, 7, 8, 9, 10, 11, 12, 13, 14, 15, 16, 17, 18, 19 or 20 L of air/minute, in a further embodiment about 15 L of air per minute. Airflow may be calibrated for example using a rotameter. In embodiments, for a given sampling, air is drawn for about 5-20 minutes, in a further embodiment for about 10-20 minutes, in a further embodiment for about 10-15 minutes, in further embodiments for about 5, 6, 7, 8, 9, 10, 11, 12, 13, 14, 15, 16, 17, 18, 19 or 20 minutes, in a further embodiment for about 15 minutes. In an embodiment, air is drawn for about 15 minutes at a flow rate of about 15 L per minute, so that a total of about 225 liters of air is drawn through the sampling device for a sampling. The sample collected in the trap is then examined (e.g. by light microscopy and/or PCR) to determine the presence and identification of the pathogen present in the sample.

In embodiments, the present invention is useful to prevent pathogen establishment and development even before a pathogen has spread to a cultural area of interest.

Sample Analysis

Collected samples are analyzed to identify and/or quantify the spores collected. In an embodiment, the samples are collected in the sampling cassette directly onto a glass slide, which can be used for microscopy analysis. Microscopic methods to examine spores (e.g., via standard staining methods such as lactic acid cotton blue or lactophenol cotton blue), count spores arid identify spores of fungal or fungal-like organisms are well known in the art. For example, various morphological features of spores and associated fungal/fungal-like structures (e.g., hyphae, etc.) may be used for identification to identify the type of pathogen.

Quantification of spores may be performed by spore counting methods, which are known in the art (see for example "Caractérisation et dénombrement des spores de moisissures prelevées par impaction sur cassette", published by the Institut de recherche en sante et en securité du travail du Québec (IRSST), 2008, ISBN: 978-2-89631-219-1 [https://www.irsst.qc.ca/media/documents/PubIRSST/M-367.pdf]; see also U.S. Pat. No. 6,692,553 and references cited therein). For example, to obtain the number of spores/m$^3$, the following formula may be used:

$$\text{spores/m}^3 = \frac{N}{(L/1000)}$$

Where: N=number of spores counted for a particular species

L=volume of air that passed through the cassette during sampling (e.g., 225 L for an airflow of 15 L/min and a duration of 15 minutes).

Culture or DNA-based methods may also be used for spore identification. DNA-based methods include amplification-based methods such as FOR methods, in which spores are identified using specific FOR sequence primers that can distinguish between organisms, Primer pairs which selectively amplify DNA only from the fungal or fungal-like species for which they are specific are known in the art for various fungal and fungal-like species or can be readily determined with only routine experimentation. Product(s) obtained by PCR amplification can be detected by visualizing the product(s) as band(s) following agarose or polyacrylamide gel electrophoresis and staining with an appropriate dye (e.g., ethidium bromide) or using fluorescent probes in a RT-PCR reaction. The identity and specificity of the PCR product(s) can be further optionally confirmed by performing DNA sequencing on the PCR products. Methods for such PCR-based identification are known in the art (see, e.g., published patents/patent applications U.S. Pat. No. 7,659,067, U.S. Pat. No. 7,291,465 and WO 2007062442)

"Amplification" refers to any in vitro procedure for obtaining multiple copies ("amplicons") of a target nucleic acid sequence or its complement or fragments thereof. In vitro amplification refers to production of an amplified nucleic add that may contain less than the complete target region sequence or its complement. In vitro amplification methods include, e.g., transcription-mediated amplification, replicase-mediated amplification, polymerase chain reaction (PCR) amplification, ligase chain reaction (LCR) amplification and strand-displacement amplification (SDA including multiple strand-displacement amplification method (NISDA)). Replicase-mediated amplification uses self-replicating RNA molecules, and a replicase such as Qβ-replicase (e.g., Kramer et al., U.S. Pat. No, 4,786,600). PCR amplification is well known and uses DNA polymerase, primers and thermal cycling to synthesize multiple copies of the two complementary strands of DNA or cDNA (e.g., Mullis et al., U.S. Pat. Nos. 4,683,195, 4,683,202, and 4,800,159). LCR amplification uses at least four separate oligonucleotides to amplify a target and its complementary strand by using multiple cycles of hybridization, ligation, arid denaturation (e.g., EP Pat. App. Pub. No. 0320308). SDA is a method in which a primer contains a recognition site for a restriction endonuclease that permits the endonuclease to nick one strand of a hemimodified DNA duplex that includes the target sequence, followed by amplification in a series of primer extension and strand displacement steps (e.g., Walker et al., U.S. Pat. No. 5,422,252). Two other known strand-displacement amplification methods do not require endonuclease nicking (Dattagupta et al., U.S. Pat. No. 6,087,133 and U.S. Pat. No. 6,124,120 (MSDA)). Those skilled in the art will understand that the spore identification methods described herein may utilize any in vitro amplification method based on primer extension by a polymerase (e.g., see Kwoh et al., 1000, Am. Biotechnol, Lab, 8:14 25 and Kwoh et al., 1989, *Proc. Natl. Acad. Sci. USA* 86, 1173 1177; Lizardi et al., 1988, BioTechnology 6:1197 1202; Malek et al., 1994, *Methods Mol. Biol.*, 28:253 260; and Sambrook et al., 2000, *Molecular Cloning—A Laboratory Manual*, Third Edition, CSH Laboratories). As commonly known in the art, the oligos are designed to bind to a complementary sequence under selected conditions. The terminology "amplification pair" or "primer pair" refers herein to a pair of oligonucleotides (oligos) which are selected to be used together in amplifying a selected nucleic acid sequence by one of a number of types of amplification processes.

Weather Parameters

Weather parameters are collected for the agricultural area of interest via a weather station installed in proximity to the agricultural area of interest. In embodiments, the weather parameters include temperature, humidity, rainfall. In embodiments, further weather parameters include wind speed, wind direction, dewpoint, and pressure. In a preferred embodiment the weather station transmits such weather parameter data wirelessly in real time, allowing for rapid access of such weather parameter data remotely and also allows for the determination of the duration (i.e., period of time in which it is continuous) of each weather parameter. Such weather stations are commercially available (e.g., from Spectrum Technologies, Libelium, and Acurite) and are well known in the art. Such weather stations may for example include one or more of a temperature sensor, humidity sensor, rain gauge, wind vane, wind cup, soil temperature sensor and soil humidity sensor.

The weather parameters are collected and categorized to determine whether they satisfy certain pre-defined criteria. Specific criteria can be defined for a given pathogen of interest. Such criteria include:

Temperature: Within a certain pre-defined range or being greater or less than and/or equal to a pre-defined level.

Humidity: % relative humidity a certain pre-defined range or being greater or less than and/or equal to a pre-defined level.

Rainfall: presence or absence, or level/amount thereof falling within a certain pre-defined range or being greater or less than and/or equal to a pre-defined level.

Time/duration: The duration of each criterion may also be assessed, i.e., that the criterion is satisfied in a continuous manner over a certain period of time. The relative moment of occurrence of each criterion may also be assessed, e.g., that the criterion is satisfied during a particular time of day, e.g., a particular window of time during a typical 24 h cycle.

Risk Assessment

The identification of spores is then combined with the analysis of local weather parameters by software to produce a risk assessment or risk index for each pathogen-based plant disease.

In an embodiment, the risk assessment regarding weather data assumes the presence of a significant inoculum for the disease of interest and is then compared to its corresponding spore capture analysis. In a further embodiment, the likelihood of the presence of an inoculum is estimated using existing predictive weather models (e.g. Journal of Plant Pathology (2009), 91 (3), 535-548, Plant disease, 88: 695-702, Phytopathology 85(5)) or models derived from retrospective data compilation and is then compared to its corresponding spore capture analysis. In an embodiment, the weather parameters are used to predict the primary infection, germination, maturation, sporulation, secondary infection (if applicable), maturation and/or sporulation. In an embodiment, the weather parameters are used to evaluate the number of generation for a given pathogen. In an embodiment, the weather parameters are analyzed and used to determine if the pre-defined criteria are satisfied, thereby generating a score for each condition to be met to generate a risk assessment. Typically, if the combination of condition scores is not met, the resulting risk assessment of pathogen infection will be low. An example of such a determination is as follows, for risk assessment of *Phytophthora infestans* in potato (this and other examples are provided in the Examples below):

Pathogen identification (from spore sampling/analysis): *Phytophthora infestans*

Weather Parameters:

| Conditions (score) | Criteria |
|---|---|
| 1 | Temp: 12 ≤ T < 18° C. |
| 2 | Temp: 18 ≤ T ≤ 24° C. |
| 3 | Temp: 24 < T ≤ 28° C. |
| 4 | humidity (%): ≥90 or leaf wetness |
| 5 | criterion continuous for at least 5 h during last 36 h |

Combination of Scores to Determine Risk Assessment:

| Conditions | Risk |
|---|---|
| 2 + 4 + 5 | high |
| 1 + 4 + 5 | medium |
| 3 + 4 + 5 | medium |
| otherwise (i.e., absence of above combinations) | low |

The risk assessments may be interpreted as follows:

LOW: Conditions are not favorable for pathogen development.

MEDIUM: Conditions are only partially favorable for pathogen development.

HIGH: Conditions are favorable for pathogen development; intervention/treatment (e.g., pesticide (e.g. fungicide) application) may be appropriate.

In embodiments, a temperature that fulfills a condition of being favorable for pathogen development is 4-24° C. (i.e., 4≤T≤24° C.), 12-25° C., 18-24° C., 20-25° C., 21-26° C., 22-25° C., 22-30° C., or 25-30° C.

In embodiments, a temperature (T) that fulfills a condition of being only partially favorable for pathogen development is 12≤T≤18° C., 24≤T≤28° C., 12≤T<21° C., 26<T≤33° C., 12≤T<22° C., 25<T≤33° C., 15≤T<25° C., T>30° C., 5≤T<20° C., 25<T≤30° C., 5≤T<22° C., 30<T≤36° C., 8≤T<12° C., or 25<T≤33° C.

In embodiments, a humidity level that fulfills a condition of being favorable for pathogen development is at least 75%, at least 90% or at least 92%.

In embodiments, a continuous duration of a temperature or humidity level described herein is at least 2, 3, 4, 5, 6, 7, 8, 9 or 10 hours, for example during a period of 36 hours. In an embodiment, a continuous duration of a temperature or humidity level described herein occurs during the period of midnight to 6 AM, for example from 2 AM to 6 AM.

In an embodiment, the pathogen is *Phytophthora infestans,* the plant is potato, and the determination and risk assessment is based on the following criteria and scores:

| *Phytophthora infestans* | | | |
|---|---|---|---|
| Conditions (score) | Criteria | Conditions | Risk |
| 1 | Temp: 12 ≤ T < 18° C. | 2 + 4 + 5 | high |
| 2 | Temp: 18 ≤ T ≤ 24° C. | 1 + 4 + 5 | medium |
| 3 | Temp: 24 < T ≤ 28° C. | 3 + 4 + 5 | medium |
| 4 | humidity (%): ≥90 or leaf wetness | otherwise | low |
| 5 | criterion continuous for at least 5 h during last 36 h | | |

In an embodiment, the pathogen is of the genus *Alternaria*, the plant is potato, and the determination and risk assessment are based on the following criteria and scores:

| Condition (score) | Criteria | Conditions | Risk |
|---|---|---|---|
| *Alternaria solani/alternata* | | | |
| 1 | Temp: $12 \leq T < 21°$ C. | 2 + 4 + 5 | high |
| 2 | Temp: $21 \leq T \leq 28°$ C. | 1 + 4 + 6 | high |
| 3 | Temp: $28 < T \leq 33°$ C. | 3 + 4 + 6 | high |
| 4 | humidity (%): ≥90 or leaf wetness | 1 + 4 + 5 | medium |
| 5 | criterion continuous for at least 5 h during last 36 h | 3 + 4 + 5 | medium |
| 6 | criterion continuous for at least 10 h during last 36 h | otherwise | low |

In an embodiment, the pathogen is of the genus *Botrytis*, the plant is potato, and the determination and risk assessment are based on the following criteria and scores:

| Conditions (score) | Criteria | Conditions | Risk |
|---|---|---|---|
| *Botrytis cinerea* | | | |
| 1 | Temp: $10 \leq T < 15°$ C. | 2 + 4 + 6 | high |
| 2 | Temp: $15 \leq T \leq 25°$ C. | 2 + 4 + 5 | medium |
| 3 | Temp: $25 < T \leq 30°$ C. | 1 + 4 + 6 | medium |
| 4 | humidity (%): ≥90 or leaf wetness | 1 + 4 + 7 | High |
| 5 | criterion for at least 10 h during last 36 h | 3 + 4 + 7 | High |
| 6 | criterion for at least 18 h during last 36 h | 1 + 4 + 6 | Medium |
| 7 | criterion for at least 26 h during last 36 h | 3 + 4 + 6 | Medium |
| | | otherwise | low |

In an embodiment, the pathogen is of the genus *Stemphylium*, the plant is onion, and the determination and risk assessment are based on the following criteria and scores:

| Conditions (score) | Criteria | Conditions | Risk |
|---|---|---|---|
| *Stemphylium* | | | |
| 1 | Temp: $10 \leq T < 17°$ C. | 2 + 4 + 5 | high |
| 2 | Temp: $17 \leq T \leq 25°$ C. | 1 + 4 + 5 | medium |
| 3 | Temp: $25 < T \leq 30°$ C. | 3 + 4 + 5 | medium |
| 4 | humidity (%): ≥90 or leaf wetness | 2 + 4 + 6 | medium |
| 5 | Criterion continuous for 10 h | Otherwise | low |
| 6 | Criterion continuous for 6 h | | |

In an embodiment, the pathogen is of the genus *Alternaria*, the plant is onion, and the determination and risk assessment are based on the following criteria and scores:

| Conditions (score) | Criteria | Conditions | Risk |
|---|---|---|---|
| *Alternaria* | | | |
| 1 | Temp: $5 \leq T < 22°$ C. | 2 + 5 + 6 | high |
| 2 | Temp: $22 \leq T \leq 30°$ C. | 1 + 5 + 6 | medium |
| 3 | Temp: $30 < T \leq 36°$ C. | 3 + 5 + 6 | medium |
| 4 | humidity (%): $80 \leq H < 90$ | 2 + 4 + 6 | medium |
| 5 | humidity (%): ≥90% or leaf wetness | otherwise | low |
| 6 | criterion continuous for at least 5 h during last 36 h | | |

In an embodiment, the pathogen is of the genus *Botrytis*, the plant is onion, and the determination and risk assessment are based on the following criteria and scores:

| Conditions (score) | Criteria | Conditions | Risk |
|---|---|---|---|
| *Botrytis* | | | |
| 1 | Temp: $10 \leq T < 15°$ C. | 2 + 4 + 6 | high |
| 2 | Temp: $15 \leq T \leq 25°$ C. | 2 + 4 + 5 | medium |
| 3 | Temp: $25 < T \leq 30°$ C. | 1 + 4 + 6 | medium |
| 4 | humidity (%): ≥90 or leaf wetness | 1 + 4 + 7 | High |
| 5 | criterion for at least 10 h during last 36 h | 3 + 4 + 7 | High |
| 6 | criterion for at least 18 h during last 36 h | 1 + 4 + 6 | Medium |

In an embodiment, the pathogen is of the genus *Peronospora*, the plant is onion, and the determination and risk assessment are based on the following criteria and scores:

| Conditions (score) | Criteria | Conditions | Risk |
|---|---|---|---|
| *Peronospora* | | | |
| 1 | Temperature: ≥30° C. for 2 h | 1 | low |
| 2 | Temperature: ≥28° C. for 6 h | 2 | low |
| 3 | Temperature: ≥27° C. for 8 h | 3 | low |
| 4 | Temperature (° C.): $4 \leq T \leq 24$ | 4 + 5 + 7 + 8 | medium |
| 5 | humidity (%): ≥90% or leaf wetness | 4 + 5 + 7 + (−8) | high |
| 6 | humidity (%): ≥92% or leaf wetness | otherwise | low |
| 7 | criterion continuous from 2 AM to 6 AM | | |
| 8 | rain: presence = 8; absence = (−8) | | |

In embodiments, the pathogen is *Alternaria dauci*, or *Cercospora carotae*, the plant is carrot, and the determinations and risk assessments are based on the following criteria and scores:

| Conditions (score) | Criteria | Conditions | Risk |
|---|---|---|---|
| *Alternaria dauci* | | | |
| 1 | Temp: $16 \leq T \leq 25°$ C. | 1 + 2 + 5 | high |
| 2 | humidity (%): ≥90 or leaf wetness | 2 + 4 + 3 | high |
| 3 | criterion continuous for at least 10 h during last 36 h | 2 + 3 | medium |
| 4 | Temp: $14 \leq T \leq 34°$ C. | 2 + 5 + 4 | medium |
| 5 | criterion continuous for at least 7 h during last 36 h | 1 + 2 + 6 | medium |
| 6 | criterion continuous for at least 4 h during last 36 h | otherwise | low |

Cercospora carotae

| Conditions (score) | Criteria | Conditions | Risk |
|---|---|---|---|
| 1 | Temp: 20 ≤ T ≤ 30° C. | 1 + 2 + 3 | high |
| 2 | humidity (%): ≥90 at least or leaf wetness | 2 + 4 + 5 | High |
| 3 | Continuous for 8 hours | 4 + 2 + 3 | Medium |
| 4 | Temp: 16 ≤ T ≤ 34° C. | 2 + 5 | Medium |
| 5 | Continuous for 12 hours | otherwise | low |

In embodiments, the pathogen is *Erysiphe necator* or *Plasmopara viticola*, the plant is grapevines, and the determinations and risk assessments are based on the following criteria and scores:

Erysiphe necator

| Conditions (score) | Criteria | Conditions | Risk |
|---|---|---|---|
| 1 | Temp average 20-27° C. | 1 + 2 + 4 | High |
| 2 | Temp average 10-34° C. | 1 + 2 + 3 + 4 | Medium |
| 3 | Temp >34° C. | 2 + 4 | Medium |
| 4 | Criterion continuous for 6 hrs for 3 consecutive days | 2 + 3 + 4 | Medium |
| 5 | Criterion continuous for 6 hrs for 2 consecutive days | 1 + 5 | Medium |
| 6 | Criterion continuous for 6 hrs in 3 of last 7 days | 1 + 6 | Medium |

Plasmopara viticola

| Conditions (score) | Criteria | Conditions | Risk |
|---|---|---|---|
| 1 | Temp: 18 ≤ T ≤ 28° C. | 1 + 4 | high |
| 2 | Temp: 12 ≤ T ≤ 18° C. | 2 + 4 | medium |
| 3 | Temp: 29 ≤ T ≤ 32° C. | 3 + 4 | medium |
| 4 | Rain between 00:00 and 7:00 | 1 + 5 + 6 | High |
| 5 | humidity (%): ≥94% or leaf wetness | 1 + 5 + 7 | High |
| 6 | Criterion continuous for 2 h between 00:00 and 7:00 | 2 + 5 + 7 | High |
| 7 | Criterion continuous for 4 h in the last 24 h | 2 + 5 + 6 | Medium |
| 8 | Criterion continuous for 8 h in the last 24 h | 3 + 5 + 7 | Medium |
|  |  | 5 + 8 | Medium |

In an embodiment, the risk assessment is determined within 4 days (96 hrs) of sampling, in a further embodiment, within 3 days (72 hrs) of sampling, in a further embodiment, within 2 days (48 hrs) of sampling, in a further embodiment, within 1 day (24 hrs) of sampling, in a further embodiment, on the same day of sampling.

Therefore, there is provided, referring to FIG. 1A, a system 10 for microbiological assessment of pathogens in an agricultural area 12 adapted to cultivate at least one plant or crop variety 14. The system 10 includes:
 a pathogen collector 16 (also referred to herein as a sampling device) for capturing pathogens or associated structures thereof in the agricultural area 12;
 pathogen identifying means 18 for identifying the pathogen captured by the pathogen collector 16;
 a weather station 20 for collecting weather data in proximity of the agricultural area 12;
 a controller 122, which may be embodied by multifunctional device 100 described below and illustrated in FIGS. 2A and 2B, comprising a processor 120 and a memory 102 configured to:
  receive pathogenic identification data that is obtained from the pathogen identifying means 18;
  receive weather data collected from the weather station 20;
  calculating a risk assessment of pathogen infection or disease of the plant or crop variety 14 based on the pathogenic identification data and the weather data; and
  transmitting an output containing the risk assessment for display 112 to a user.

In the system, the risk assessment is calculated in real-time when both the pathogenic spore data is generated and the weather data is collected so as to provide a user and/or robotic systems with reliable and time dependent information.

Figure 1B:
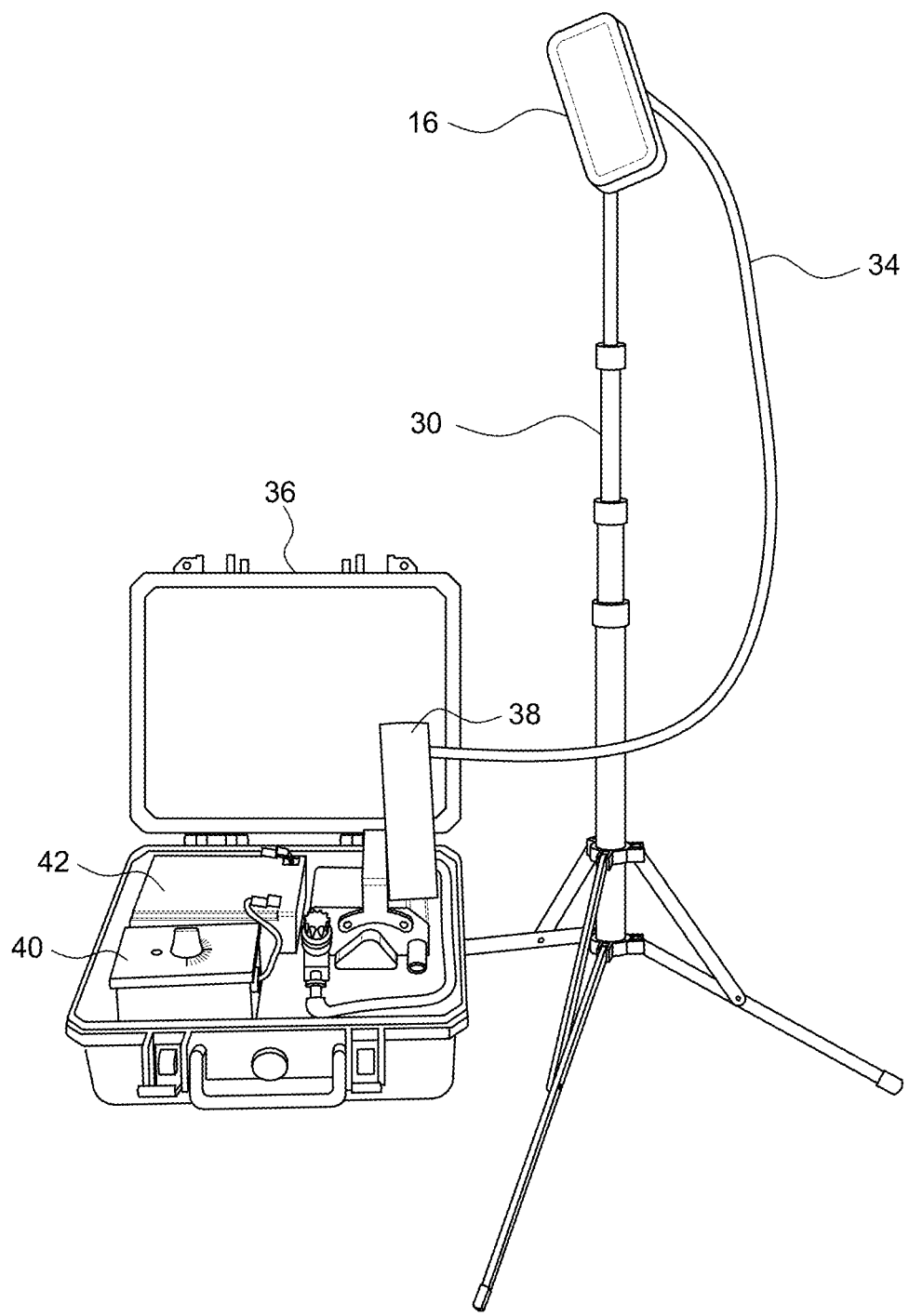
FIGS. 1B and 1C are perspective views of elements used in a pathogen management system, according to a preferred embodiment of the present invention.
Figure 1C:
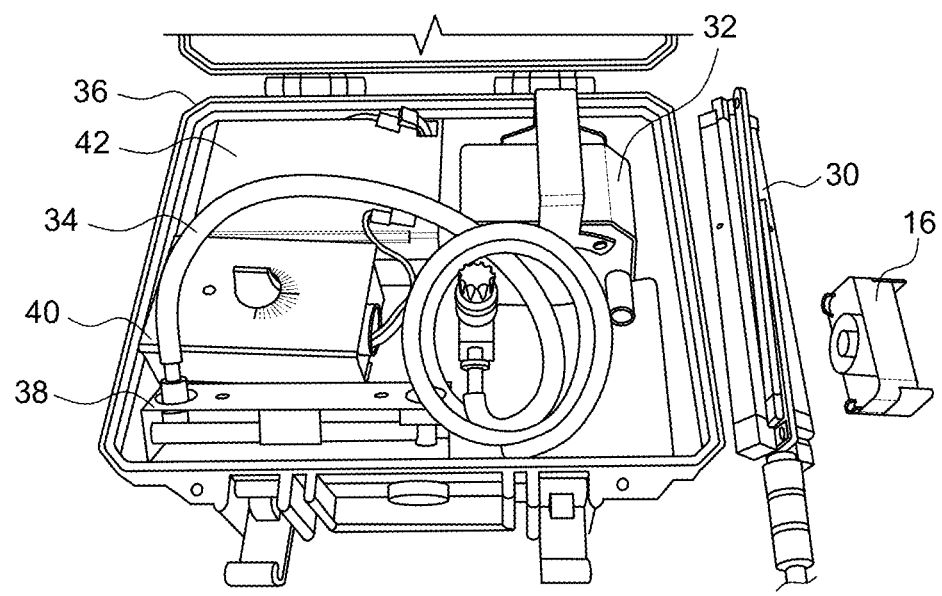

Referring now to FIGS. 1B and 1C, in addition to FIG. 1A, the pathogen collector 16, also called cassette or sampling device, may be mounted on a tripod 30 and is connected to an air pump 32 via flexible tube 34 for assisting in the collection of pathogen spores in the agricultural area 12. The pathogen collector 16, tripod 30, air pump 32 and the flexible tube 34 may be conveniently packed as a kit in a suitcase 36, and thus be portable to facilitate convenient packup, movement and setup for sampling at multiple locations. Also enclosed in the suitcase 36 may be a flowmeter 38 for measuring the flow rate of the air passing through the pathogen collector 16 via air pump 32. Also enclosed in the suitcase 36 may be a timer 40 for measuring the time that the pathogen collector 16 is used. Also enclosed in the suitcase 36 may be a battery 42 for providing power to the air pump 32.

Figure 1D:
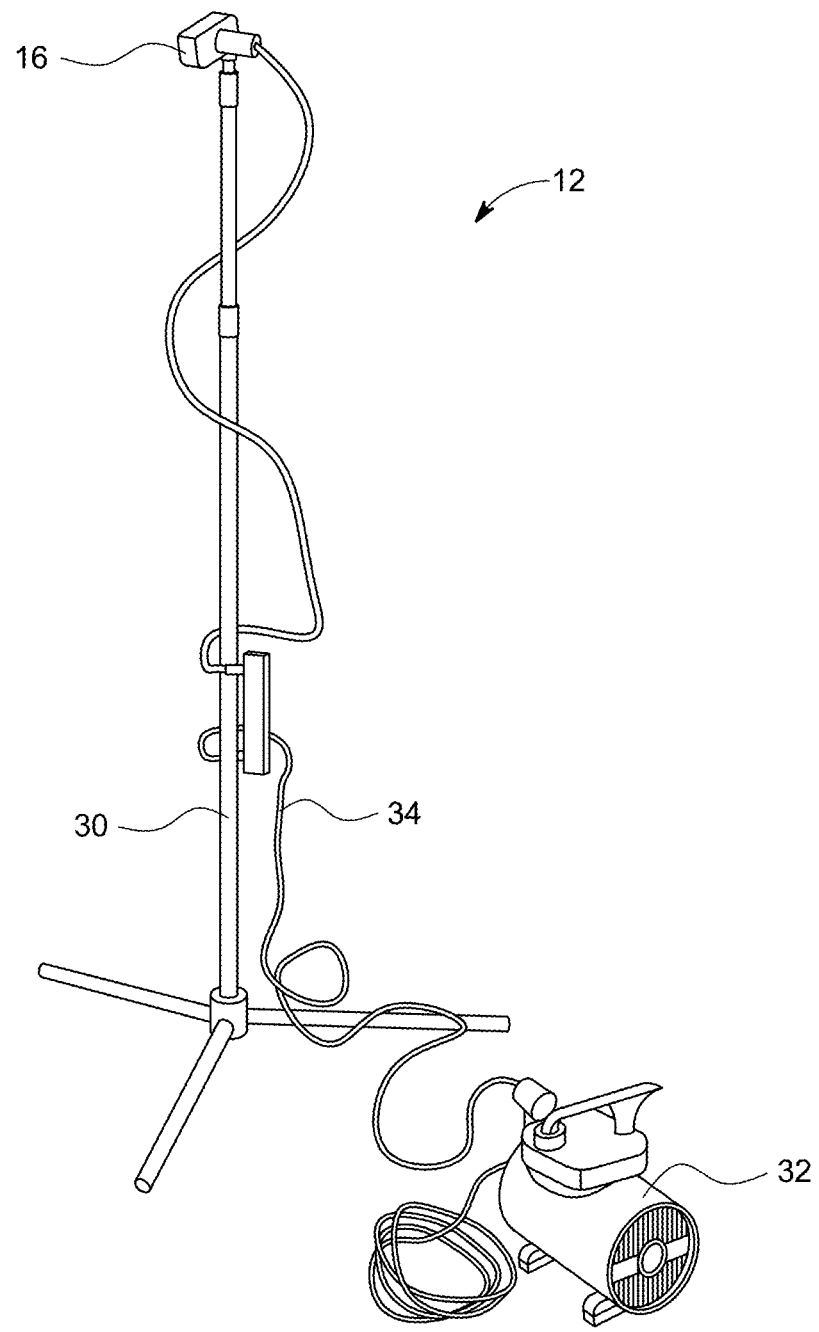
FIG. 1D is a perspective view of elements used in a pathogen management system, according to a preferred embodiment of the present invention.

Referring now to FIG. 1D, in addition to FIGS. 1A to 1C, there is shown the pathogen collector 16 mounted on tripod 30 and connected to larger air pump 32 via flexible tube 34 for assisting in the collection of pathogen spores in the agricultural area 12.

As described herein, the pathogen collector 16 may be
 Allergenco-D cassette
 Jet-spore impactor
 Air-O-Cell cassette
 Cyclex-D cassette
 Micro 5 cassette
 Rotorod sampler
 Burkard type captor/sampler As described herein, the pathogen identifying means 18 may include any apparatus used to identify the pathogenic spores in the agricultural area 12. These apparatuses include microscopes, microscopes slides/coverslips, stains/staining agents.

As described herein the weather station 20 is for measuring weather data such as temperature, humidity, air pressure, wind speed, rain, soil humidity, etc. Such weather stations may for example include one or more of a temperature sensor, humidity sensor, rain gauge, wind vane, wind cup, soil temperature sensor and soil humidity sensor.

In an embodiment, there is also provided a method for microbiological assessment of pathogens in an agricultural area 12 adapted to cultivate at least one plant or crop variety 14, including;
 capturing pathogenic spores by means of a pathogen collector 16 in the agricultural area 12;
 identifying the pathogen captured by the pathogen collector 16 and generating pathogen identification data;
 collecting weather data in proximity of the agricultural area 12;

calculating a risk assessment of pathogen infection or disease to the plant or crop variety 14 based on the pathogen identification data arid the weather data; and informing a user of the risk assessment.

In the method, the risk assessment is calculated in real-time with respect to generating the pathogenic spore data and collecting the weather data so as to provide a user and/or robotic systems with reliable and time dependent information.

Referring back to FIG. 1A, there is also provided is a system for microbiological assessment and suppression of pathogens in an agricultural area 12 adapted to cultivate at least one plant or crop variety 14, including a pathogen collector 16 for capturing pathogen or associated structures thereof in the agricultural area 12;

pathogen identifying means 18 for identifying the pathogenic spores captured by the pathogen collector 16;

a weather station 20 for collecting weather data in proximity of the agricultural area 12;

a controller 122 which may be embodied by multifunctional device 100 described below and illustrated in FIGS. 2A and 2B, comprising processor 120 and memory 102 configured to:

receive pathogenic identification data that is obtained from the pathogen identifying means 16;

receive weather data collected from the weather station 20;

calculating a risk assessment of pathogen infection or disease of the plant or crop variety 14 based on the pathogenic identification data and the weather data;

transmitting spore data and the weather data;

pathogenic control means 22 for application of an anti-pathogenic substance to the agricultural area 12 or a portion thereof such that it comes in contact with the at least one plant or crop variety 14 or the soil or air proximal thereto, based on the risk assessment.

As described herein, the pathogenic control means 22 may include automatic sprinklers that spray the anti-pathogenic substance in the agricultural area 12 that comes into contact with the plant or crop variety 14. Of course, pathogenic control means 22 may include aerial spray system such as planes or drones or manual hoses, as known in the art.

Representative examples of risk determination for potato, onion, carrot and grapevines are shown in the Examples below. However, the methods and system described herein can easily be adapted and used for a wide variety of plants, such as those described herein). Further, the methods and systems may be utilized to perform the risk assessment for a variety of plant pathogens. Any disease associated with a type of spores with recognizable morphological characteristics can be recognized by this method. To adapt the method to a new culture, the formulas of the package are simply modified according pathogenic spores interest proliferation and weather factors specific to that particular culture.

Risk Assessment Display

Embodiments of electronic devices, user interfaces for such devices, and associated processes for using such devices in conjunction with the display of pathogen of risk assessment are described. In some embodiments, the device is a portable communications device, such as a mobile telephone or smart mobile phone, that also contains other functions, such as a PDA. Exemplary embodiments of portable multifunction devices include, without limitation, the iPhone®, iPod Touch®, and iPad® devices from Apple Inc. (e.g., iOS devices). Other embodiments of portable electronic devices include Android devices. Other portable electronic devices, such as laptops or tablet computers with touch-sensitive surfaces (e.g., touch screen displays and/or touchpads), may be used. It should also be understood that, in some embodiments, the device is not a portable communications device, but is a desktop computer with or without a touch-sensitive surface. The electronic device may optionally include one or more other physical user-interface devices, such as a physical keyboard, a mouse, etc. In a further embodiment, the user-interface may be a voice-activated/responsive interface.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Referring to FIG. 2A, there is shown a block diagram illustrating a portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110 connected to a speaker and microphone, input/output (I/O) subsystem 106, and other input control devices 116. Device 100 optionally includes one or more optical sensors 164. Device 100 optionally includes one or more tactile output generators 167 for generating tactile outputs on device 100 (e.g., generating tactile outputs on a touch-sensitive surface such as touch-sensitive display system 112 of device 100). These components optionally communicate over one or more communication buses or signal lines 103.

It should be appreciated that device 100 is only one example of a portable multifunction device, and that device 100 optionally has more or fewer components than shown, optionally combines two or more components, or optionally has a different configuration or arrangement of the components. The various components shown in FIG. 2A are implemented in hardware, software, or a combination of both hardware and software, including one or more signal processing and/or application-specific integrated circuits.

Memory 102 may include one or more computer-readable storage mediums. The computer-readable storage mediums may be tangible and non-transitory. Memory 102 may include high-speed random access memory and may also include non-volatile memory, such as one or more magnetic disk storage devices, flash memory devices, or other non-volatile solid-state memory devices. Memory controller 122 may control access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 may be implemented on a single chip, such as chip 104. In some other embodiments, they may be implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA-F, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BILE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP). Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110 connected to speaker and microphone provide an audio interface between a user and device 100. Audio circuitry 110 receives audio data from peripherals interface 118, converts the audio data to an electrical signal, and transmits the electrical signal to speaker as known in the art. Speaker converts the electrical signal to human-audible sound waves. Audio circuitry 110 also receives electrical signals converted by microphone from sound waves. Audio circuitry 110 converts the electrical signal to audio data and transmits the audio data to peripherals interface 118 for processing. Audio data may be retrieved from and/or transmitted to memory 102 and/or RF circuitry 108 by peripherals interface 118.

I/O subsystem 106 couples input/output peripherals on device 100, such as touch screen 112 and other input control devices 116, to peripherals interface 118. I/O subsystem 106 optionally includes display controller 156, optical sensor controller 158, haptic feedback controller 160, and one or more input controllers 161 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 161 are, optionally, coupled to any (or none) of the following: a keyboard, an infrared port, a USB port, and a pointer device such as a mouse.

Touch-sensitive display 112 provides an input interface and an output interface between the device and a user. Display controller 156 receives and/or sends electrical signals from/to touch screen 112. Touch screen 112 displays visual output to the user. The visual output may include graphics, text, icons, video, and any combination thereof (collectively termed "graphics"). In some embodiments, some or all of the visual output may correspond to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Device 100 may also include one or more optical sensors 164. FIG. 2A shows an optical sensor coupled to optical sensor controller 158 in I/O subsystem 106. Optical sensor 164 may include charge-coupled device (CCD) or complementary metal-oxide semiconductor (CMOS) phototransistors. Optical sensor 164 receives light from the environment, projected through one or more lenses, and converts the light to data representing an image.

Device 100 optionally also includes one or more tactile output generators 167. FIG. 2A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device).

In some embodiments, the software components stored in memory 102 include operating system 126, communication module (or set of instructions) 128, graphics module (or set of instructions) 132, text input module (or set of instructions) 134, and applications (or sets of instructions) 136.

Operating system 126 (e.g., Darwin. RTXC, LINUX, UNIX. OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports and also includes various software components for handling data received by RF circuitry 108 and/or external port.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which may be a component of graphics module 132, provides soft keyboards for entering text in various applications (e.g., contacts, e-mail, IM 141, browser 147, and any other application that needs text input).

Applications 136 may include many different modules (or sets of instructions), or a subset or superset thereof, such as a telephone module 138, e-mail module 140, browser module 147, etc., and widget modules 149 such as calculator module 150, etc.

In particular, pathogen management module 152 can be used to provide to a user a risk assessment of pathogen infection and related disease in plants or crops in the agricultural area.

Figure 2A:
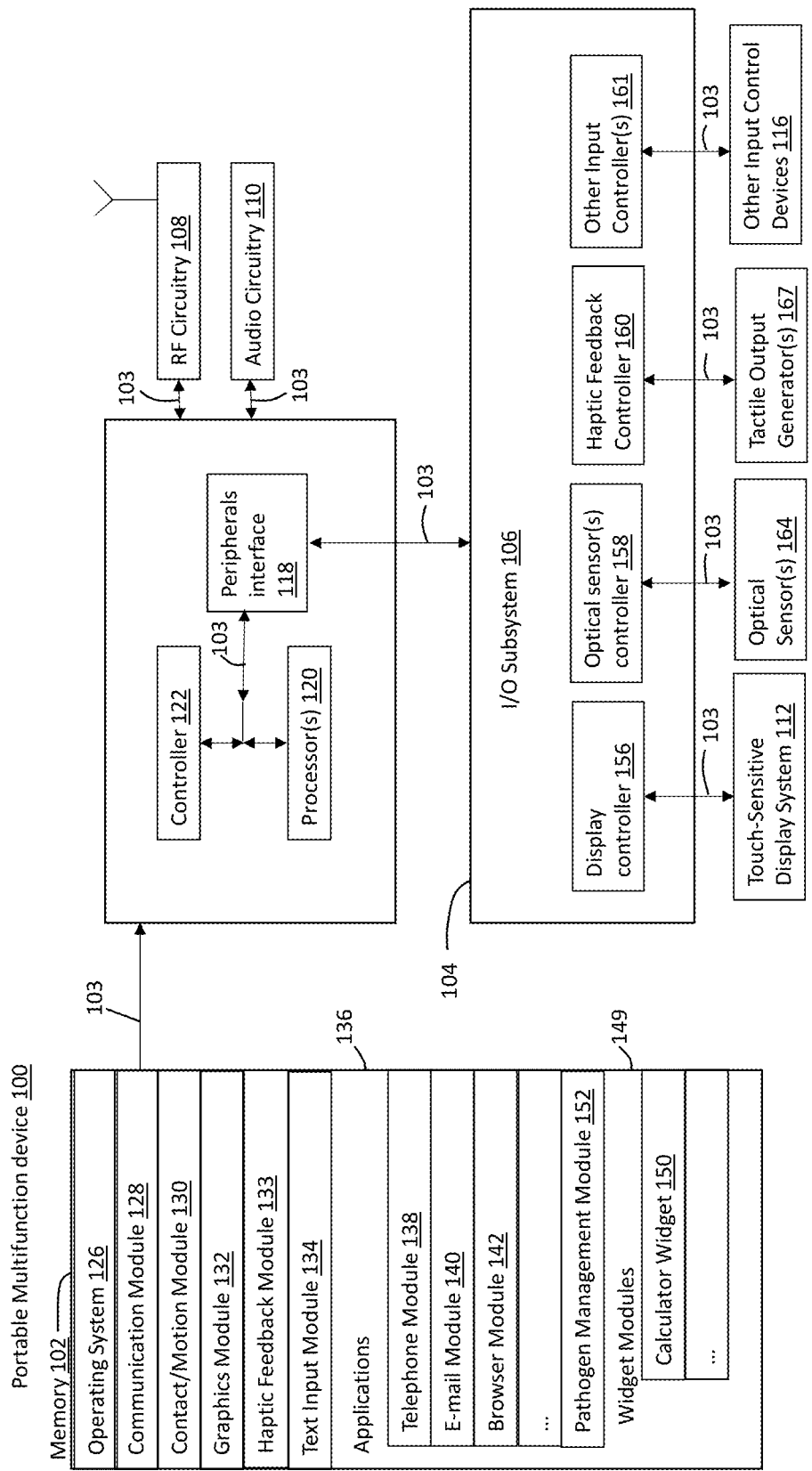
FIG. 2A is a block diagram of a multifunctional device used in a pathogen management system, according to a preferred embodiment of the present invention.
Figure 2B:
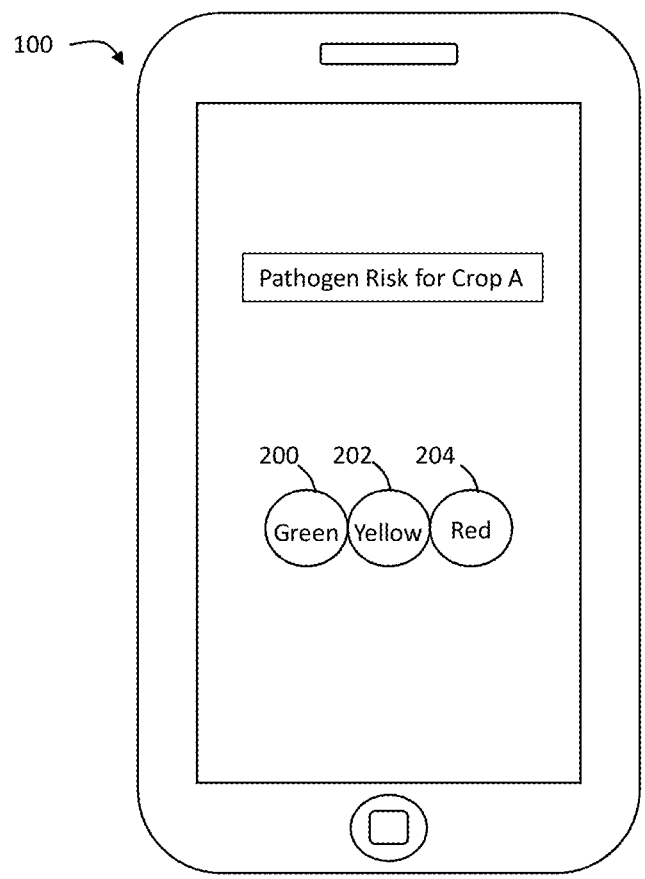
FIG. 2B is a front view of a multifunctional device used in a pathogen management system, according to a preferred embodiment of the present invention.

FIG. 2B illustrates an exemplary user interface for displaying a risk assessment pathogen infection and related disease in plants or crops in an agricultural area that is being monitored. For example, the display of device 100 in conjunction with pathogen management module 152 are used to display to a user the pathogen risk to a particular crop A located in a given agricultural area by means of graphical illustrations such that when the risk is assessed to be low a green circle 200 is displayed, when the risk is assessed to be medium a yellow circle 202 is displayed, and when the risk is assessed to be high a red circle 204 is displayed. Of course other graphical and/or text can be used to provide the risk assessment to the user and is only one of the ways that a client may be informed about risk assessment. More generally, the user or user client may access the same risk assessment information either by using a dedicated application or by using a web interface such as a remote access customer center link either via a smart phone or a computer. In the client account customer link, the user may browse different analysis reports that may be generated as pdf files. On each report, every type of spore that is present may be clearly quantified and the computer or smart phone may display a green, yellow or red circle corresponding to the level of risk associated with the weather data.

Figure 2C:
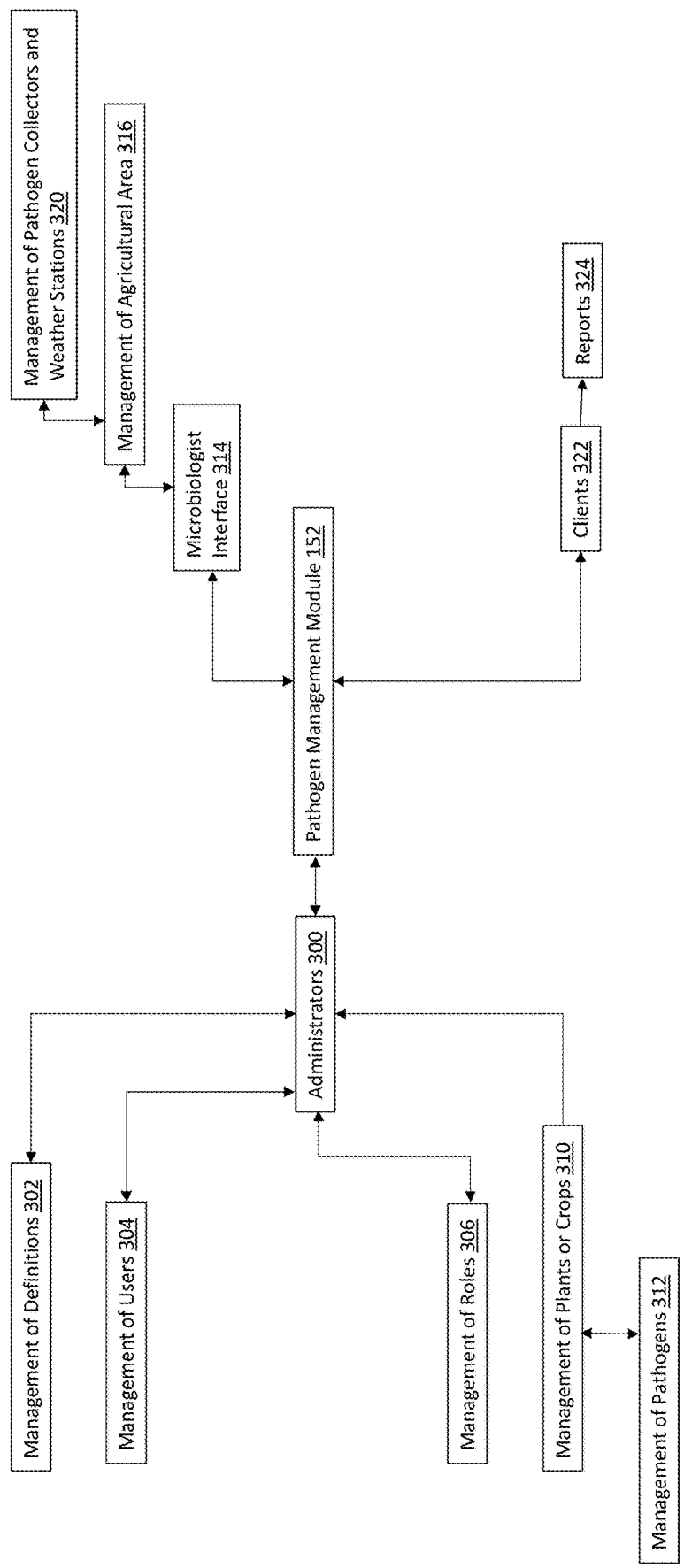
FIG. 2C is a block diagram of an application architecture for a multifunctional device used in a pathogen management system, according to a preferred embodiment of the present invention.

FIG. 2C illustrates a more detailed view of a mobile application architecture that is associated with the pathogen management module 152 shown in FIG. 2A. The pathogen management module 152 may be managed via an administrator interface 300. The administrator interface 300 is linked to a management of definitions module 302 that is used to create, modify and suppress all the different definitions of the application. These definitions describe precisely each of the pathogens, which may be selected by the microbiologist so that these may be automatically included in a pdf report that is referred to below. The administrator interface 300 is also linked to a management of user module 304 that is used to create, modify and suppress users of the application. The management of user module 304 may assign a role to a particular user that is created or modified. The administrator interface 300 is also linked to a management of roles module 306 that is used create, modify and suppress roles that are assigned by the administration modules. The roles correspond to different access rights that are granted to the different users. In the illustrated example, the roles are those of administrator, biologist and client. The administrator role has typically the highest access rights to the application so that the administrator may create, modify and suppress any of the data contained in the pathogen management application. The access rights to the microbiologist are typically more limited and are related to the microbiologist interface module 314 described below. The access right to the clients are typically more limited and are related to the client module 320 that is described below. The administrator interface 300 is also linked to a management of plants or crops module 310 that is used to create, modify and suppress the different types of plants or crops in the application. The management of plants or crops module 310 is in turn linked to a management of pathogens module 312 that is used to create, modify and suppress the different pathogens associated with the different plants or crops. The management of pathogens module 312 may be used to modify criteria and levels associated to each pathogen. The criteria are established according to the assessment of risk of proliferation of pathogens, which are typically ranked as low, medium and high and are determined as described in the present application with respect to temperature ranges, humidity levels, time duration, time of day, rain conditions, wind speed, direction of speed, etc. The pathogen management module 152 is also linked to a microbiologist interface module 314 that is used to manage the different clients of the application. The microbiologist interface module 314 may be used to create, modify and suppress different clients of the pathogen management application. The microbiologist interface module 314 is linked to a management of agricultural area module 216 that is used to create, modify and suppress the different agricultural areas associated with each client. The management of agricultural area module 216 is linked to a management of the pathogen collectors and weather stations module 320 that is associated to the different pathogen collectors 16 and weather stations 20 of an agricultural area 12 that are shown in FIG. 1A for any given client. The management of the pathogen collectors and weather stations module 320 is used to create, modify and suppress the different pathogen collectors and weather stations in the pathogen management application. The management of the pathogen collectors and weather stations module 320 may also be used to enter the pathogen data and weather data in the pathogen management application. The management of the pathogen collectors and weather stations module 320 may also be used to generate reports by performing the different risk assessment calculations that are described further herein. The pathogen management module 152 is also linked to a client module 322 that is used to generate and send risk assessment reports to a client via a report module 324. These reports may be pdf files providing different risk assessments and recommendations to a client associated to an agricultural area 12 with plants or crops 14 shown in FIG. 1A.

FIG. 3 illustrates an exemplary report of a risk assessment of pathogen infection and related disease in plants or crops in an agricultural area that is being monitored. The report is transmitted or made available to a user that can be located in a remote location with respect to the agricultural area that is monitored. The interface for displaying the report may be part of any device that is online or connected to the internet or via any other communications means. The risk assessment report is generated in real-time as soon as the pathogenic spore data and weather data that are received.

Treatment

The risk assessment or report described herein may be used to direct application of a suitable pesticide(s) to counter the identified pathogen(s). For example, as noted above, such treatment is recommended and may be performed if a high risk assessment is obtained. Fungicides, herbicides and insecticides are all pesticides used in plant protection. In an embodiment, the pesticide used for treatment is a fungicide. Thus in an embodiment, the methods described herein further comprise selecting a pesticide (e.g., fungicide) to be applied to the agricultural area in accordance with the risk report. In a further embodiment, the methods described herein further comprise applying a pesticide (e.g., fungicide) to the agricultural area (e.g., to the soil, plants or air thereof) in accordance with the risk assessment or report.

A fungicide is a specific type of pesticide that controls disease caused by fungi or fungus-like organisms (e.g. oomycete), by specifically inhibiting or killing the fungus or fungus-like organism causing the disease. Diseases caused by other types of organisms, disorders caused by abiotic factors, and insect damage are not controlled by fungicides. Thus it is ideal to first determine the cause of symptoms or risk thereof before applying a fungicide. Fungicides are used not only to control a disease during crop growth, but also to increase crop productivity and reduce blemishes. For example, leaf damage due to disease can reduce photosynthesis, and blemishes can affect the food portion of a crop or affect the appearance of ornamentals. Diseases can also affect the storage and quality of harvested plants and produce (e.g., resulting in increased spoilage of food crops post-harvest). Most fungicides are ideally applied before disease occurs or at the first appearance of symptoms to be effective.

Fungicides are applied most often as liquid, but also as dust, granules and gas. In the field, they are for example applied to (1) soil, either in-furrow at planting, after planting as a soil drench (e.g., drip irrigation), or as a directed spray around the base of the plant; (2) foliage and other aboveground parts of plants via spraying; (3) in gaseous form in the air in enclosed areas such as greenhouses and covered soil. Post-harvest, they may be applied to harvested produce for example via dipping or spraying.

Commonly used fungicides include, for example, thiophanate-methyl, iprodione, vinclozolin, triflumizole, triforine, myclobutanil, tebuconazole, mefenoxam, carboxin, cyprodinil, azoxystrobin, trifloxystrobin, pyraclostrobin, fludioxonil, quintozene, dicloran, and etridiazole. In embodiments, the fungicide is a phosphonate fungicide, which is effective for example against oomycetes. Numerous fungicides for various pathogens and associated plant diseases are well known in the art. Further examples of fungicides include boscalide, cyazofamide, metiram, ametoctradine, dimethomorphe, fluoxastrobine, difenoconazole, penthiopyrade, chlorothalonile, fluopyram (which are for example commonly used in potato horticulture).

The present invention is illustrated in further details by the following non-limiting examples.

EXAMPLE 1

Agricultural Field Sampling

Materials:
Allergenco-D cassette (sampling cassette)
Pump and Rotameter
Portable power source (optional)
Tripod
Timer
Method:
The sampling assembly is positioned such that the wind passes over the area of interest before reaching the sampling location. Preferably, care is taken to minimize raising dust near the sampling location.
The height of the sampling assembly is adjusted so that the sampling cassette is about 0.15 m above the foliage, and at least 1 m above the ground.
The pump is attached to the cassette.
The flow rate is adjusted to 15 L/min.
The seal (typically an adhesive cover or sticker) is removed (and retained) from the capture orifice of the cassette, and the pump is activated.
Sampling is performed for a sufficient time, typically about 10-20 minutes (e.g., 10 or 15 minutes), during which time freezing and UV exposure is avoided.
The pump is stopped and the seal is re-applied to the capture orifice of the cassette.
Samples may be stored at ambient temperature, and are typically subjected to laboratory analysis within 5 days.

EXAMPLE 2

Sample Analysis

Sample preparation
Materials:
Allergenco-D slide
Optical microscope (e.g., with 40× and 100× objectives)
Immersion oil
Cover slip
Manual counter
Lactic acid cotton blue stain
A wet mount of the sample is performed and stained with lactic acid cotton blue.
Sample Examination
Spores are counted at 400× magnification (10× ocular and 40× objective). Spore characteristics are studied at 1000× (10× ocular and 100× objective; oil immersion) for identification. Identification may optionally be supplemented by PCR analysis, which entails removal of spores from the capture device to perform DNA extraction. PCR primers are chosen in accordance with the pathogen to be identified. PCR products are typically analyzed by agarose gel electrophoresis and ethidium bromide staining.

Calculation:

To obtain the number of spores/m³, the following formula is used:

$$\text{spores/m}^3 = \frac{N}{(L/1000)}$$

Where: N=number of spores counted for a particular species

L=volume of air that passed through the cassette during sampling (e.g.,225 L for an airflow of 15 L/min and a duration of 15 minutes).

Determination of Risk Level

The interpretation of the spore sampling results is based on the air passing over the fields in the window of time involving the release of more spores of interest, mainly oomycetes. Spores are identified on the basis of theft unique morphology. The absence of spores causing a particular disease suggests low or absence of inoculum and thus, lower risk.

In parallel, weather data is collected in the proximity of the field where the aft sampling takes place, via an installed weather station.

As a weather station is installed at each site, weather data is col ected that is specific to the site. The station will transmit temperature, atmospheric pressure, relative humidity and rainfall continuously to a server via a Wi-Fi connection. The combination of the air sampling data and the weather data is used to generate a risk index of the proliferation of agricultural pathogens. Sample risk index determinations for certain agricultural pathogens and crops are as follows:

Potato

*Phytophthora infestans*

| Conditions (score) | Criteria | Conditions | Risk |
|---|---|---|---|
| 1 | Temp: 12 ≤ T < 18° C. | 2 + 4 + 5 | high |
| 2 | Temp: 18 ≤ T ≤ 24° C. | 1 + 4 + 5 | medium |
| 3 | Temp: 24 < T ≤ 28° C. | 3 + 4 + 5 | medium |
| 4 | humidity (%): ≥90 or leaf wetness | otherwise | low |
| 5 | criterion continuous for at least 5 h during last 36 h | | |

*Alternaria solani/alternata*

| Condition (score) | Criteria | Conditions | Risk |
|---|---|---|---|
| 1 | Temp: 12 ≤ T < 21° C. | 2 + 4 + 5 | high |
| 2 | Temp: 21 ≤ T ≤ 28° C. | 1 + 4 + 6 | high |
| 3 | Temp: 28 < T ≤ 33° C. | 3 + 4 + 6 | high |
| 4 | humidity (%): ≥90 or leaf wetness | 1 + 4 + 5 | medium |
| 5 | criterion continuous for at least 5 h during last 36 h | 3 + 4 + 5 | medium |
| 6 | criterion continuous for at least 10 h during last 36 h | otherwise | low |

*Botrytis cinerea*

| Conditions (score) | Criteria | Conditions | Risk |
|---|---|---|---|
| 1 | Temp: 10 ≤ T ≤ 15° C. | 2 + 4 + 6 | high |
| 2 | Temp: 15 ≤ T ≤ 25° C. | 2 + 4 + 5 | medium |
| 3 | Temp: 25 < T ≤ 30° C. | 1 + 4 + 6 | medium |
| 4 | humidity (%): ≥90 or leaf wetness | 1 + 4 + 7 | High |
| 5 | criterion for at least 10 h during last 36 h | 3 + 4 + 7 | High |
| 6 | criterion for at least 18 h during last 36 h | 1 + 4 + 6 | Medium |
| 7 | criterion for at least 26 h during last 36 h | 3 + 4 + 6 | Medium |
| | | otherwise | low |

Onion

*Stemphylium*

| Conditions (score) | Criteria | Conditions | Risk |
|---|---|---|---|
| 1 | Temp: 10 ≤ T ≤ 17° C. | 2 + 4 + 5 | high |
| 2 | Temp: 17 ≤ T ≤ 25° C. | 1 + 4 + 5 | medium |
| 3 | Temp: 25 < T ≤ 30° C. | 3 + 4 + 5 | medium |
| 4 | humidity (%): ≥90 or leaf wetness | 2 + 4 + 6 | medium |
| 5 | Criterion continuous for 10 h | otherwise | low |
| 6 | Criterion continuous for 6 h | | |

*Alternaria*

| Conditions (score) | Criteria | Conditions | Risk |
|---|---|---|---|
| 1 | Temp: 5 ≤ T < 22° C. | 2 + 5 + 6 | high |
| 2 | Temp: 22 ≤ T ≤ 30° C. | 1 + 5 + 6 | medium |
| 3 | Temp: 30 < T ≤ 36° C. | 3 + 5 + 6 | medium |
| 4 | humidity (%): 80 ≤ H < 90 | 2 + 4 + 6 | medium |
| 5 | humidity (%): ≥90% or leaf wetness | otherwise | low |
| 6 | criterion continuous for at least 5 h during last 36 h | | |

*Botrytis*

| Conditions (score) | Criteria | Conditions | Risk |
|---|---|---|---|
| 1 | Temp: 10 ≤ T < 15° C. | 2 + 4 + 6 | high |
| 2 | Temp: 15 ≤ T ≤ 25° C. | 2 + 4 + 5 | medium |
| 3 | Temp: 25 < T ≤ 30° C. | 1 + 4 + 6 | medium |
| 4 | humidity (%): ≥90 or leaf wetness | 1 + 4 + 7 | High |
| 5 | criterion for at least 10 h during last 36 h | 3 + 4 + 7 | High |
| 6 | criterion for at least 18 h during last 36 h | 1 + 4 + 6 | Medium |

*Peronospora*

| Conditions (score) | Criteria | Conditions | Risk |
|---|---|---|---|
| 1 | Temperature: ≥30° C. for 2 h | 1 | low |
| 2 | Temperature: ≥28° C. for 6 h | 2 | low |
| 3 | Temperature: ≥27° C. for 8 h | 3 | low |
| 4 | Temperature (° C.): 4 ≤ T ≤ 24 | 4 + 5 + 7 + 8 | medium |

Peronospora

| Conditions (score) | Criteria | Conditions | Risk |
|---|---|---|---|
| 5 | humidity (%): ≥90% or leaf wetness | 4 + 5 + 7 + (−8) | high |
| 6 | humidity (%): ≥92% or leaf wetness | otherwise | low |
| 7 | criterion continuous from 2 AM to 6 AM | | |
| 8 | rain: presence = 8; absence = (−8) | | |

Carrot

Alternaria dauci

| Conditions (score) | Criteria | Conditions | Risk |
|---|---|---|---|
| 1 | Temp: 16 ≤ T ≤ 25° C. | 1 + 2 + 5 | high |
| 2 | humidity (%): ≥90 or leaf wetness | 2 + 4 + 3 | high |
| 3 | criterion continuous for at least 10 h during last 36 h | 2 + 3 | medium |
| 4 | Temp: 14 ≤ T ≤ 34° C. | 2 + 5 + 4 | medium |
| 5 | criterion continuous for at least 7 h during last 36 h | 1 + 2 + 6 | medium |
| 6 | criterion continuous for at least 4 h during last 36 h | otherwise | low |

Cercospora carotae

| Conditions (score) | Criteria | Conditions | Risk |
|---|---|---|---|
| 1 | Temp: 20 ≤ T ≤ 30° C. | 1 + 2 + 3 | high |
| 2 | humidity (%): ≥90 at least or leaf wetness | 2 + 4 + 5 | High |
| 3 | Continuous for 8 hours | 4 + 2 + 3 | Medium |
| 4 | Temp: 16 ≤ T ≤ 34° C. | 2 + 5 | Medium |
| 5 | Continuous for 12 hours | otherwise | low |

Grapevines

Erysiphe necator (secondary infection)

| Conditions (score) | Criteria | Conditions | Risk |
|---|---|---|---|
| 1 | Temp average 20-27° C. | 1 + 2 + 4 | High |
| 2 | Temp average 10-34° C. | 1 + 2 + 3 + 4 | Medium |
| 3 | Temp >34° C. | 2 + 4 | Medium |
| 4 | Criterion continuous for 6 hrs for 3 consecutive days | 2 + 3 + 4 | Medium |
| 5 | Criterion continuous for 6 hrs for 2 consecutive days | 1 + 5 | Medium |
| 6 | Criterion continuous for 6 hrs in 3 of last 7 days | 1 + 6 | Medium |

Plasmopara viticola

| Conditions (score) | Criteria | Conditions | Risk |
|---|---|---|---|
| 1 | Temp: 18 ≤ T ≤ 28° C. | 1 + 4 | high |
| 2 | Temp: 12 ≤ T ≤ 18° C. | 2 + 4 | medium |
| 3 | Temp: 29 ≤ T ≤ 32° C. | 3 + 4 | medium |
| 4 | Rain between 00:00 and 7:00 | 1 + 5 + 6 | High |
| 5 | humidity (%): ≥94% or leaf wetness | 1 + 5 + 7 | High |
| 6 | Criterion continuous for 2 h between 00:00 and 7:00 | 2 + 5 + 7 | High |
| 7 | Criterion continuous for 4 h in the last 24 h | 2 + 5 + 6 | Medium |
| 8 | Criterion continuous for 8 h in the last 24 h | 3 + 5 + 7 | Medium |
| | | 5 + 8 | Medium |

EXAMPLE 3

Examples of Risk Determination

EXAMPLE 3A

Potato

Samples: I

Air volume: 225 L

Sampling, receipt of sample at laboratory, analysis of sample, determination of risk and preparation of risk report all performed on the same day.

Limit of detection: 4 spores/m$^3$

Potato—*Phytophthora infestans*—sample 3A-I -Weather station data:

Temperature fulfilled criteria of 18≤T≤24° C. (score 2) for at least 5 h (score 5); humidity fulfilled criteria of 90% (score 4). Resulting risk assessment of high (2+4+5).

Potato—*Alternaria*—sample 3A-I -Weather station data:

Temperature fulfilled criteria of 12≤T<21° C. (score 1) for at least 5 h (score 5); humidity fulfilled criteria of ≥90% (score 4). Resulting risk assessment of medium (1+4+5).

Potato—*Botrytis*—sample 3A-I -Weather station data:

Temperature fulfilled criteria of 15≤T<25° C. (score 2) for at least 10 h (score 5); humidity fulfilled criteria of 90% (score 4). Resulting risk assessment of medium (2+4+5).

Results of risk determination are shown below:

| | | Mold and/or bacteria | | Quantity (spores/m$^3$) | | | |
|---|---|---|---|---|---|---|---|
| Sample | Debris* | Identification | Associated disease | Previous | | Current | Risk |
| 3A-I | 0 | *Phytophthora infestans* | Mildew | ND | ND | 49 | high |
| | | *Alternaria solani/alternata* | Early blight | 67 | 129 | 53 | medium |
| | | *Fusarium* spp. | *Fusarium* disease/rot | ND | ND | ND | low |
| | | *Botrytis cinerea* | Gray rot | ND | ND | ND | medium |

*Density of debris - legend: 0: no debris 1-2: trace amount of debris; no or very little interference 3-4: significant amount of debris; interference possible 5: too much debris; analysis impossible; sample unsuitable for analysis

EXAMPLE 3B

Potato and Onion

Samples: potato and onion

Air volume: 225 L

Sample received at laboratory 3 days after sampling, and analysis of sample, determination of risk and preparation of risk report all performed on day that the sample was received at the laboratory. Limit of detection: 4 spores/m$^3$ Potato—*Phytophthora infestans*—Weather station data:

Temperature fulfilled criteria of 18≤T≤24° C. (score 2) for at least 5 h (score 5); humidity fulfilled criteria of 90% (score 4). Resulting risk assessment of high (2+4+5).

Potato—*Alternaria*—Weather station data:

Temperature fulfilled criteria of 21≤T≤28° C. (score 2) for at least 5 h (score 5); humidity fulfilled criteria of 90% (score 4). Resulting risk assessment of high (2+4+5).

Potato—*Botrytis*—Weather station data:

Temperature fulfilled criteria of 15<T≤25° C. (score 2) for at least 10 h (score 5); humidity fulfilled criteria of 90% (score 4). Resulting risk assessment of medium (3+4+5).

Onion—*Alternaria*—Weather station data:

Temperature fulfilled criteria of 30<T≤36° C. (score 3) for at least 5 h (score 6); humidity fulfilled criteria of ≥90% (score 5). Resulting risk assessment of medium (3+5+6).

Onion—*Botrytis*—Weather station data:

Temperature fulfilled criteria of 15≤T≤25° C. (score 2) for at least 18 h (score 6); humidity fulfilled criteria of 90% (score 4). Resulting risk assessment of high (2+4+6).

Onion—*Peronospora*—Weather station data:

Temperature fulfilled criteria of ≥30° C. for 2 h (score 1). Resulting risk assessment of low (1).

Results of risk determination are shown below:

| | | Mold and/or bacteria | | Quantity (spores/m$^3$) | | | |
|---|---|---|---|---|---|---|---|
| Sample | Debris* | Identification | Associated disease | Previous | | Current | Risk |
| 3B- | 0 | *Phytophthora infestans* | Mildew | ND | ND | ND | high |
| potato | | *Alternaria solani/alternata* | Early blight | ND | ND | 80 | high |
| | | *Fusarium* spp. | *Fusarium* disease/rot | ND | ND | 4 | low |
| | | *Botrytis cinerea* | Gray rot | ND | ND | ND | medium |
| 3B- | 0 | *Alternaria porri* | Early blight | ND | ND | 73 | medium |
| onion | | *Botrytis squamosa* | Gray rot | ND | ND | ND | high |
| | | *Peronospora destructor* | Mildew | ND | ND | ND | low |
| | | *Fusarium* spp. | *Fusarium* disease/rot | ND | ND | 4 | low |

*Density of debris - legend: see Example 3A

EXAMPLE 3C

Carrot

Sample: I
Air volume: 225 L
Sampling, receipt of sample at laboratory, analysis of sample, determination of risk and preparation of risk report all performed on the same day.
Limit of detection: 4 spores/m$^3$
Carrot—*Alternaria dauci*—Weather station data:
Temperature fulfilled criteria of 16≤T≤25° C. (score 1) for at least 4 h (score 6); Humidity did not fulfill criteria of 90% for at least 24 h (thus no score 2); Resulting risk assessment of low (otherwise low).
Carrot—*Gercospora carotae*—Weather station data:
Temperature fulfilled criteria of 16≤T≤34° C. (score 4); Humidity fulfill criteria of ≥90% (score 2); criterion not continuous for 8 h. Result risk assessment low (Otherwise low).
Results of risk determination are shown below:

| | | Mold and/or bacteria | | Quantity (spores/m$^3$) | | | |
|---|---|---|---|---|---|---|---|
| Sample | Debris* | Identification | Associated disease | Previous | | Current | Risk |
| 3C-1 | 0 | *Erysiphe heraclei* | Mildew | ND | ND | ND | medium |
| | | *Cercospora carotae* | *Cercospora* leaf blight | ND | 44 | 116 | low |
| | | *Alternaria dauci* | *Alternaria* disease (leaf blight) | ND | 18 | 636 | low |

*Density of debris - legend: see Example 3A

EXAMPLE 3D

Grapevines

Samples: I
Air volume: 225 L
Sampling, receipt of sample at laboratory, analysis of sample, determination of risk and preparation of risk report all performed on the same day.
Grapevines—*Erysiphe nectator*—Weather station data:
Average temperature criterion not fulfilled Resulting risk assessment of low (otherwise low)
Grapevines—*Plasmopara viticola*—Weather station data:
Temperature fulfilled criterion of 18≤T≤28° C. (score 1); for at least 4h in the last 24 h (score 7) Humidity does not fulfill criteria of ≥94% (score 5) ; Resulting risk assessment of low (otherwise low).
Results of risk determination are shown below:

| | | Mold and/or bacteria | | Quantity (spores/m$^3$) | | | |
|---|---|---|---|---|---|---|---|
| Sample | Debris* | Identification | Associated disease | Previous | | Current | Risk |
| 3D-I | 0 | *Erysiphe necator* | Powdery mildew | ND | ND | ND | Low |
| | | *Alternaria alternata* | *Alternaria* disease (leaf blight) | ND | ND | 80 | Low |
| | | *Botrytis cinerea* | Gray rot | ND | ND | 4 | Low |
| | | *Plasmopora viticoia* | Mildew | ND | ND | ND | Low |

*Density of debris - legend: see Example 3A

Although the present invention has been described hereinabove by way of preferred embodiments thereof, it can be modified, without departing from the spirit and nature of the subject invention as defined in the appended claims.

The invention claimed is:

1. A method to determine a risk for infection by a spore of interest in a plant in an agricultural area, comprising:
    (a) providing a weather station configured to continuously collecting weather data, the weather data comprising a measurement of at least one of temperature and humidity in the agricultural area;
    (b) providing a spore collector located in the agricultural area and configured to collect a spore;
    (c) providing an apparatus for identifying the collected spore as the spore of interest; and
    (d) providing a controller configured to:
        (i) receive data comprising the identification data of (c);
        (ii) receive and analyze the collected weather data to determine whether the weather data satisfy pre-defined criteria, each criterion specific to the spore of interest, wherein the criteria comprise the occurrence of at least one of the temperature being within a pre-defined range and for a first pre-determined continuous duration and the percent humidity being within a pre-defined range and for a second pre-determined continuous duration, wherein the first and second durations are at least 2 hours;
        (iii) determine the risk for infection of a plant in the agricultural area by the spore of interest as low, medium, or high based on the combination of satisfied criteria of step (ii); and
        (iv) transmit an output containing the risk for infection by the spore of interest for display to a user.

2. The method of claim 1, wherein the plant is a tuber, or potato, or of the genus *Allium,* or an onion or a grapevine or a carrot and wherein the spore is from a fungus or a fungus-like organism or ascomycete, or a basidiomycete or a deuteromycete or an oomycete or a phytomoxea.

3. The method of claim 1, wherein the spore is collected by impaction at an airflow of about 10 to about 20 L air/minute and wherein the spore collector is configured to collect the spore for a period of about 5 to about 20 minutes.

4. The method of claim 1, wherein the apparatus for identifying the spore of interest is configured to identify the spore by optical microscopy or by an amplification method.

5. The method of claim 1, wherein the weather data further comprises one or more of (i) rainfall, (ii) pressure, (iii) dewpoint, (iv) continuous duration of any one of (i)-(iv), or (v) time of day of occurrence of any one of (i)-(iv).

6. The method of claim 1, wherein the weather data further comprise the time of day of occurrence of any one of temperature being within a pre-defined range and for a first pre-determined continuous duration and the percent humidity being within a pre-defined range and for a second pre-determined continuous duration.

7. The method of claim 1, wherein the risk for infection is calculated in a remote location relative to the user or the agricultural area.

8. The method of claim 1, wherein the user is located in a remote location relative to the agricultural area.

9. The method of claim 1, wherein the spore collector is positioned in the agricultural area such that the wind passes over at least a portion of the agricultural area before reaching the spore collector.

10. A system to determine a risk for infection by a spore of interest in a plant in an agricultural area, comprising:
 (a) a weather station configured to continuously collect weather data, the weather data comprising a measurement of at least one of temperature and humidity in the agricultural area;
 (b) a spore collector located in the agricultural area and configured to collect a spore;
 (c) an apparatus for identifying the collected spore as the spore of interest; and
 (d) a controller configured to:
  (i) receive data comprising the identification data of (c);
  (ii) receive and analyze the collected weather data to determine whether the weather data satisfy pre-defined criteria, each criterion specific to the spore of interest, wherein the criteria comprise the occurrence of at least one of the temperature being within a pre-defined range and for a first pre-determined continuous duration and the percent humidity being within a pre-defined range and for a second pre-determined continuous duration, wherein the first and second durations are at least 2 hours;
  (iii) determine the risk for infection of a plant in the agricultural area by the spore of interest as low, medium, or high based on the combination of satisfied criteria of step (ii); and
  (iv) transmit an output containing the risk for infection by the spore of interest for display to a user.

11. The system of claim 10, wherein the spore collector is part of a portable sampling kit.

12. The system of claim 10, further comprising a computer device for receiving the output of the controller, wherein the computer device is located in a remote location relative to the agricultural area.

13. The system of claim 10, wherein the plant is a tuber, or a potato, or is of the genus *Allium,* or an onion, or a grapevine or a carrot and wherein the spore is a fungus or a fungus-like organism or an ascomycete, a basidiomycete, or a deuteromycete or an oomycete or a phytomoxea.

14. The system of claim 10, wherein the spore is collected by impaction at an airflow of about 10 to about 20 L air/minute and wherein the spore collector is configured to collect the spore for a period of about 5 to about 20 minutes.

15. The system of claim 10, the apparatus for identifying the spore is located in a remote location relative to the agricultural area or to the user and wherein the controller is located in a remote location relative to the agricultural area or the user.

16. The system of claim 10, wherein the risk for infection is determined in a remote location relative to the user or to the agricultural area.

17. The system of claim 10, wherein the first and second durations are the same.

18. The system of claim 10, wherein the weather data further comprises one or more of (i) rainfall, (ii) pressure, (iii) dewpoint, (iv) continuous duration of any one of (i)-(iv), or (v) time of day of occurrence of any one (i)-(iv).

19. The method of claim 10, wherein the weather data further comprise the time of day of occurrence of any one of temperature being within a pre-defined range and for a first pre-determined continuous duration and the percent humidity being within a pre-defined range and for a second pre-determined continuous duration.

20. A system to determine risk for infection by a spore of interest in a plant in an agricultural area and suppression of spores, comprising:
 (a) a weather station configured to continuously collect weather data, the weather data comprising a measurement of at least one of temperature and humidity in the agricultural area;
 (b) a spore collector in the agricultural area and configured to collect a spore;
 (c) an apparatus for identifying the collected spore as the spore of interest; and
 (d) a controller configured to:
  (i) receive data comprising the identification data of (c);
  (ii) receive and analyze the collected weather data to determine whether the weather data satisfy pre-defined criteria, each criterion specific to the spore of interest, wherein the criteria comprise the occurrence of at least one of the temperature being within a pre-defined range and for a first pre-determined continuous duration and the percent humidity being within a pre-defined range and for a second pre-determined continuous duration, wherein the first and second durations are at least 2 hours;
  (iii) determine the risk for infection of a plant in the agricultural area by the spore of interest as low, medium, or high based on the combination of satisfied criteria of step (ii);
  (iv) transmit an output containing the risk for infection by the spore of interest for display to a user; and
 (e) an apparatus for spraying the plant with an anti-pathogenic substance based on the risk for infection.

21. The system of claim 20, wherein the apparatus for spraying the plant comprises a robotic device for receiving instructions from the controller to automatically spray the plant with the anti-pathogenic substance based on the risk for infection.

22. The system of claim 20, comprising a computer device for receiving an output of the controller containing the risk for infection, the computer device being located in a remote location relative to the agricultural area.

* * * * *